(12) United States Patent
Mallinson

(10) Patent No.: US 11,176,731 B2
(45) Date of Patent: Nov. 16, 2021

(54) FIELD OF VIEW (FOV) THROTTLING OF VIRTUAL REALITY (VR) CONTENT IN A HEAD MOUNTED DISPLAY

(71) Applicant: Sony Interactive Entertainment Inc., Tokyo (JP)

(72) Inventor: Dominic S. Mallinson, Redwood City, CA (US)

(73) Assignee: Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 16/379,732

(22) Filed: Apr. 9, 2019

(65) Prior Publication Data

US 2019/0236836 A1 Aug. 1, 2019

Related U.S. Application Data

(63) Continuation of application No. 15/471,466, filed on Mar. 28, 2017, now Pat. No. 10,255,715, which is a
(Continued)

(51) Int. Cl.
*G06T 15/20* (2011.01)
*A61B 5/392* (2021.01)
(Continued)

(52) U.S. Cl.
CPC .............. *G06T 15/20* (2013.01); *A61B 5/024* (2013.01); *A61B 5/0531* (2013.01); *A61B 5/392* (2021.01);
(Continued)

(58) Field of Classification Search
None
See application file for complete search history.

(56) References Cited

U.S. PATENT DOCUMENTS 9,583,019 B1 * 2/2017 Schwartz ................ G09B 9/16
2007/0070072 A1 * 3/2007 Templeman ............ A63F 13/00
345/473

(Continued)

OTHER PUBLICATIONS

Irving "Restricting field of view to reduce motion sickness in VR", posted online Jun. 15, 2016 @ https://newatlas.com/columbia-university-vr-motion-sickness/43855/ (Year: 2016).*

*Primary Examiner* — Yingchun He
(74) *Attorney, Agent, or Firm* — Penilla IP, APC

(57) ABSTRACT

A method for reducing discomfort when viewing virtual reality (VR) content for use in head mounted displays (HMDs). The method includes accessing a model that identifies a plurality of learned patterns associated with the generation of corresponding baseline VR content that is likely to cause discomfort. The method includes processing a first application to generate data associated with simulated user interactions with first VR content of the first application. The method includes comparing the data to the model to identify a pattern in the data matching at least one of the learned patterns, such that the identified pattern is likely to cause discomfort. The method includes identifying a zone in the first application corresponding to identified pattern. The method includes applying a discomfort reduction filter effect within the zone for purposes of reducing potential discomfort in a user.

20 Claims, 11 Drawing Sheets

Related U.S. Application Data continuation of application No. 15/372,217, filed on Dec. 7, 2016, now Pat. No. 10,565,777.

(60) Provisional application No. 62/402,963, filed on Sep. 30, 2016.

(51) Int. Cl.

| | | |
|---|---|---|
| *A61M 21/00* | (2006.01) | |
| *G02B 27/01* | (2006.01) | |
| *G02B 27/00* | (2006.01) | |
| *A61B 5/024* | (2006.01) | |
| *A61B 5/0531* | (2021.01) | |
| *G06F 3/01* | (2006.01) | |
| *G06N 3/04* | (2006.01) | |
| *G06N 3/08* | (2006.01) | |
| *G06T 19/00* | (2011.01) | |
| *A63F 13/53* | (2014.01) | |
| *G06N 3/02* | (2006.01) | |
| *G06N 5/04* | (2006.01) | |
| *G06T 19/20* | (2011.01) | |

(52) U.S. Cl.
CPC ............ *A61M 21/00* (2013.01); *A63F 13/53* (2014.09); *G02B 27/0093* (2013.01); *G02B 27/017* (2013.01); *G06F 3/011* (2013.01); *G06F 3/012* (2013.01); *G06N 3/02* (2013.01); *G06N 3/04* (2013.01); *G06N 3/08* (2013.01); *G06N 5/04* (2013.01); *G06T 19/006* (2013.01); *G06T 19/20* (2013.01); *A61M 2021/005* (2013.01); *A61M 2021/0044* (2013.01); *A61M 2205/507* (2013.01); *A61M 2230/06* (2013.01); *A61M 2230/10* (2013.01); *A61M 2230/14* (2013.01); *A61M 2230/63* (2013.01); *A61M 2230/65* (2013.01); *A63F 2300/303* (2013.01); *G02B 2027/014* (2013.01); *G06F 3/013* (2013.01); *G06F 3/015* (2013.01); *G06T 2200/04* (2013.01); *G06T 2200/24* (2013.01); *G06T 2207/20024* (2013.01); *G06T 2207/20092* (2013.01)

(56) References Cited

U.S. PATENT DOCUMENTS

| | | | | |
|---|---|---|---|---|
| 2012/0134543 | A1* | 5/2012 | Fedorovskaya | G06K 9/00 382/107 |
| 2016/0086378 | A1* | 3/2016 | Shuster | G06F 3/012 345/633 |
| 2016/0167672 | A1* | 6/2016 | Krueger | A61B 5/7282 340/576 |
| 2016/0219325 | A1* | 7/2016 | Chu | A63F 13/35 |

* cited by examiner

FIELD OF VIEW (FOV) THROTTLING OF VIRTUAL REALITY (VR) CONTENT IN A HEAD MOUNTED DISPLAY

CROSS REFERENCE TO RELATED APPLICATIONS

The present application is a continuation of and claims priority to and the benefit of commonly owned U.S. patent application Ser. No. 15/471,466, with filing date Mar. 28, 2017; which is a continuation of and claims priority to and the benefit of commonly owned U.S. patent application Ser. No. 15/372,217, with filing date Dec. 7, 2016; which claims priority to and the benefit of the U.S. Provisional Patent Application 62/402,963, with filing date Sep. 30, 2016, all of which are herein incorporated by reference in their entireties.

This application is related to commonly assigned, co-pending U.S. patent application Ser. No. 15/085,899, entitled "PERSONALIZED DATA DRIVEN GAME TRAINING SYSTEM," filed on Mar. 30, 2016, the disclosure of which is hereby incorporated by reference in its entirety.

TECHNICAL FIELD

The present disclosure is related to improving user experience when interacting with virtual reality (VR) content, and the implementation of discomfort reduction filtering effects for VR content that is likely to induce discomfort and/or sickness in a user.

BACKGROUND OF THE DISCLOSURE

Computer generated virtual reality (VR) allows a user to be immersed in a simulated real environment or an imaginary environment, for example. With complete immersion, the user is able to interact with the simulated or imaginary environment, as if the user were present within that VR environment. That is, the user is able to move and look around the VR environment, and possibly interact with objects within that VR environment.

VR systems can use some display system to let the user view the VR environment. These display systems may include a computer monitor or display screen that is presented in front of the user. When the display screen is smaller, the VR experience of the user is hampered by visual stimulation from the surrounding real environment (e.g., sunlight, objects in real space, etc.). The VR experience may be improved by increasing the display size to reduce the influence of the surrounding real environment. Further, the display system may be designed to block out stimulation from the surrounding real environment. For example, a head mounted display (HMD) worn by a user is able to block out light from the physical, real environment, and present a stereoscopic screening system to the user for viewing the VR environment in three dimensions (3D). These HMDs may include viewing goggles integrated with a mounting system that is worn on or over the head. Still other more complex VR systems may be integrated with movement sensors that allow a user to make moves in a real world that may then be translated in some form to the world of VR. For instance, hand gestures/movements may be used to interact with VR objects, and moving through the real world (e.g., walking in the physical environment) may be translated to similar movement in the VR environment (e.g., walking or running in the VR environment).

VR systems have been embraced by various industries, such as the military, real estate, medicine, video gaming, etc. Because the user can be totally immersed within a VR environment, that VR environment may simulate a real environment for purposes of training, enjoyment, and escape. For example, a VR system may be used for pilot training in the military, surgical technique training within the medical industry, showing a listing by a real estate agent, or experiencing a vacation destination. In addition, the VR environment may be used to simulate a completely imaginary environment, such as a fantasy world where characters have super human powers. For example, the user may be immersed within a video gaming VR environment that allows the user to take on the skills and movements of a gaming character within that VR environment. In that manner, the user is able to extend the margins of reality by giving the user the sense of imaginary movements and skills. This is analogous to having a disabled person feel as if he or she were able to move (e.g., walk) within the VR environment.

However, the VR experience of a user will vary with the type of VR content presented, and with the compatibility of the user for interacting with the VR content. In some cases, VR content may induce sickness or discomfort in the user that is akin to motion sickness experienced in the physical, real world. The discomfort by the user may be due in general to sensory cues (e.g., visual, auditory, etc.) that are somehow not compatible with a specific user, though research in the area has not determined exactly why these cues may or may not be compatible.

It is in this context that embodiments of the disclosure arise.

SUMMARY

Embodiments of the present disclosure relate to systems and methods for building a model through a deep learning engine that is configured for predicting discomfort of a user when interacting with VR content, for identifying zones in VR content that are likely to induce discomfort and/or sickness based on predicted discomfort of a user as determined by the model, and for applying a discomfort reduction filtering effect in those identified zones. Several inventive embodiments of the present disclosure are described below.

In one embodiment, a method for reducing discomfort when viewing virtual reality (VR) content for use in head mounted displays (HMDs) is disclosed. The method includes accessing a model that identifies a plurality of learned patterns associated with the generation of corresponding baseline VR content that is likely to cause discomfort. The method includes processing a first application to generate data associated with simulated user interactions with first VR content of the first application. The method includes comparing the extracted data to the model to identify a pattern in the extracted data matching at least one of the learned patterns, such that the identified pattern is likely to cause discomfort. The method includes identifying a zone in the first application corresponding to the identified pattern. The method includes applying a discomfort reduction filter effect within the zone for purposes of reducing potential discomfort in a user.

In one embodiment, another method for reducing discomfort when viewing virtual reality (VR) content for use in head mounted displays (HMDs) is disclosed. The method includes executing an application to generate VR content for interaction by a user. The method includes receiving an input indicating discomfort in the user. The method includes applying a discomfort reduction filter effect to VR content generated for display purposes of reducing potential discomfort.

In another embodiment, a non-transitory computer-readable medium storing a computer program for reducing discomfort when viewing VR content for use in HMDs is disclosed. The computer-readable medium includes program instructions for executing an application to generate VR content for interaction by a user. The computer-readable medium includes program instructions for receiving an input indicating discomfort in the user. The computer-readable medium includes program instructions for applying a discomfort reduction filter effect to VR content generated for display for purposes of reducing potential discomfort by applying in real-time field of view throttling as an overlay to the VR content.

Other aspects of the disclosure will become apparent from the following detailed description, taken in conjunction with the accompanying drawings, illustrating by way of example the principles of the disclosure.

BRIEF DESCRIPTION OF THE DRAWINGS

The disclosure may best be understood by reference to the following description taken in conjunction with the accompanying drawings in which.

DETAILED DESCRIPTION

Although the following detailed description contains many specific details for the purposes of illustration, anyone of ordinary skill in the art will appreciate that many variations and alterations to the following details are within the scope of the present disclosure. Accordingly, the aspects of the present disclosure described below are set forth without any loss of generality to, and without imposing limitations upon, the claims that follow this description.

Generally speaking, the various embodiments of the present disclosure describe systems and methods implementing deep learning techniques to determine which VR content induces user discomfort and/or sickness, and for classifying and/or identifying points or zones in VR content and/or the source of VR content that are likely to induce discomfort and/or sickness based on predicted user discomfort and/or sickness. In particular, embodiments of the present disclosure build a model through a deep learning engine that is configured for predicting discomfort of a user when interacting with VR content, identify zones in VR content and/or the source of the VR content that are likely to induce discomfort and/or sickness based on predicted discomfort of a user as determined by the model, and apply a discomfort reduction filtering effect in those identified zones.

With the above general understanding of the various embodiments, example details of the embodiments will now be described with reference to the various drawings.

Figure 1A:
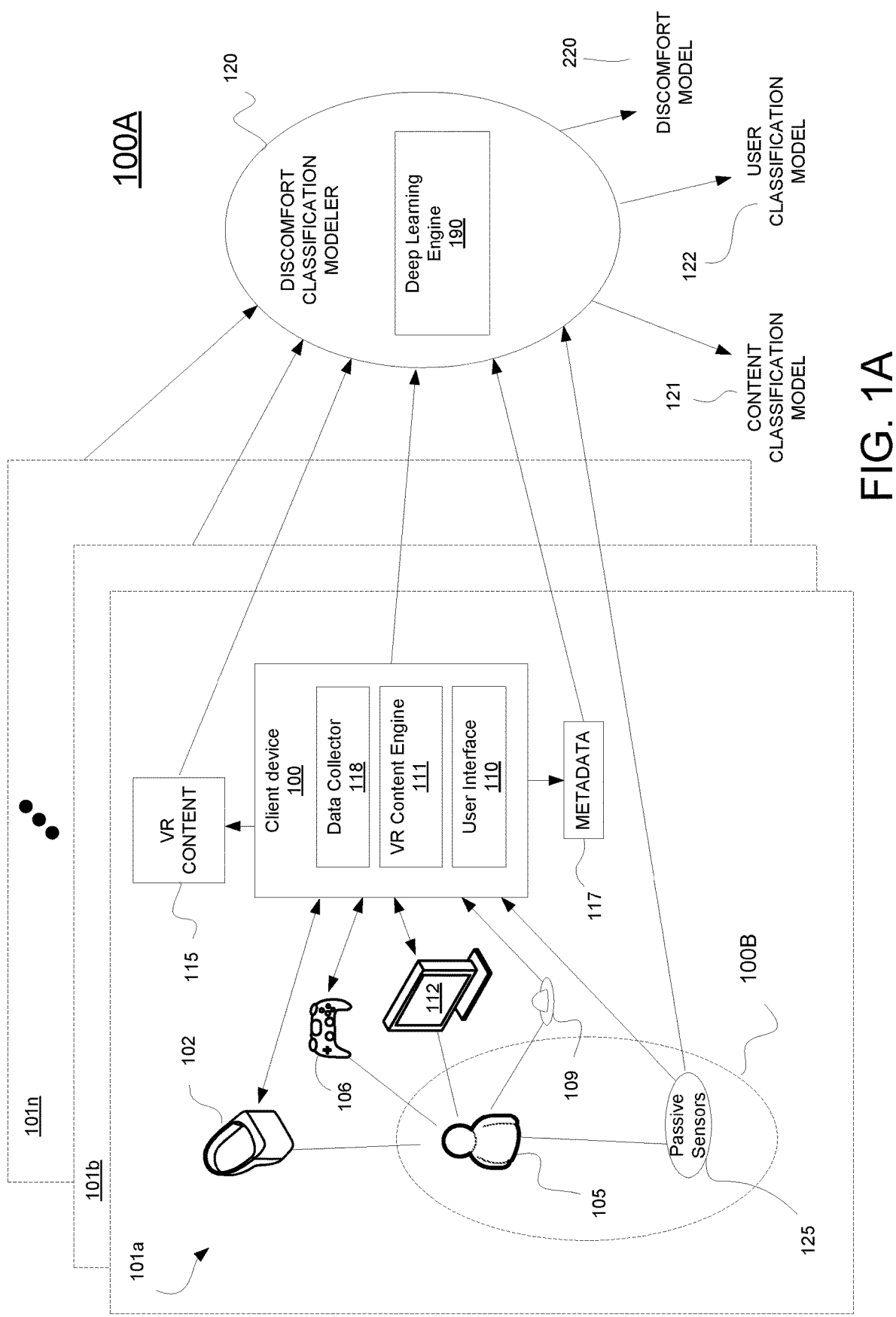
FIG. 1A illustrates a system used for building a discomfort and/or sickness recognition model through a deep learning engine that is configured for correlating discomfort of a user when interacting with VR content, in accordance with one embodiment of the present disclosure.

FIG. 1A illustrates a system 100A used for building a discomfort and/or sickness recognition model through a deep learning engine that is configured for correlating discomfort of a user when interacting with VR content, in accordance with one embodiment of the present disclosure. System 100A can be implemented in a testing environment in order to learn under what conditions users will experience discomfort and/or sickness when viewing and/or interacting with VR content, and then to apply that knowledge to build models that can be used to classify VR content (e.g., identify points in VR content likely to induce discomfort and/or sickness) based on predicted discomfort and/or sickness experienced by users when interacting with the VR content.

The testing environment includes a plurality of test users that are subjected to a plurality of VR content. Each of the test users is monitored using a corresponding test system. For illustration, test user 105 is monitored using test system 101a, and other test users are monitored using test systems 101b-101n, etc.

As a representative example of the plurality of test systems (e.g., 101a-101n), test system 101a is described to illustrate the monitoring of the test user 105 during interaction with VR content 115. The VR content 115 includes one or more baseline VR content, wherein each baseline content is associated with known or true discomfort and/or sickness responses. Further, the VR content may be of any type, including rendered images from gaming applications, videos, multimedia content, static images, etc.

Client device 100 is configured for generating the VR content 115. For example, the VR content may be generated by an application (e.g., gaming application) running on the VR content engine 111 (e.g., game execution engine). For example, the application is designed to produce images that when viewed through a corresponding display device (e.g., HMD 102 or display 112) can give a user a three-dimensional VR viewing experience. In one implementation, the client device 100 may be a stand-alone system configured to generate and/or play the VR content (e.g., execute the code of a gaming application to render images), or may request access to VR content over a network (not shown), such as the internet, or for rendering VR content received from an instance of an application (e.g., gaming application) executed by a back end server (e.g., implementing a virtual machine), and delivered to the display device 112 associated with user 105, or delivered to a head mounted display (HMD) 102 that is configured to display VR content. In some embodiments, the client device 100 may be an HMD.

Further, the client device 100 may receive input from various types of input devices, such as game controllers 106, tablet computers, keyboards, gestures captured by video cameras, mice, touch pads, etc. Client device 100 can be any type of computing device having at least a memory and a processor module that is capable of generating and/or playing the VR content 115. Some examples of client device 100 include a personal computer (PC), a game console, HMD, a home theater device, a general purpose computer, a video recording player, mobile computing device, a tablet, a phone, or any other types of computing devices that can play the VR content 115. User interface 110 may be used for playing the VR content, setting up testing, and/or used for managing the collection of data input into the discomfort classification modeler 120.

In particular, client device 100 is configured for generating and/or receiving rendered images of VR content, and for displaying the rendered images on display 112 or HMD 102. For example, the rendered images may be associated with an instance of a gaming application executing on the client device 100, or executing on a back end game server in association with user 105. In the case of interactive VR content, such as that associated with a gaming application, client device 100 is configured to interact with the instance of the video game executing on engine 111 and that is associated with game play of user 105, such as through input commands that are used to drive game play.

During the interaction by user 105 with the VR content 115, various data is monitored, wherein the data is associated with the VR content 115 (e.g., rendered images, etc.) and the user 105. The data may be monitored and collected by client device 100, or directly by the discomfort classification modeler 120. This data is input in the discomfort classification modeler 120 in order to learn the VR content and/or patterns of VR content that induce discomfort and/or sickness in users. The data includes VR content that is generated, For example, the VR content is monitored by test system 101a to recognize patterns associated with VR content that can then be correlated with data from test users that experience discomfort and/or sickness, wherein a pattern can include any type of VR content (e.g., static image, sequence of images, etc.), or patterns of actions taken or generated by the user in association with the generation of that VR content. The patterns may be associated with simulated user interactions with corresponding VR content. Over time, if the same pattern of VR content (e.g., moving horizon, avatar linear and rotational accelerations, etc.), or patterns of actions, consistently induces discomfort and/or sickness in the test users, then those patterns can be labeled as producing discomfort and/or sickness reactions in consumer users who interact with that VR content. In one embodiment, the client device 100 is configured to monitor and parse out the patterns of VR content, or patterns of actions taken or generated by the user in association with the generation of that VR content, while the VR content is being played or interacted with by the test user 105. In another embodiment, the discomfort classification modeler 120, and more specifically, the deep learning engine 190 is configured to monitor and parse out the patterns of VR content, or patterns of actions taken or generated by the user in association with the generation of that VR content, while it is being played or interacted with by the test user 105.

In addition, the test system 101a monitors physiological data associated with the test user 105 collected during interaction with VR content 115. The physiological data may be passively or actively monitored. Passive monitoring does not require help from the user, whereas active monitoring requires user help.

In particular, in one embodiment test system 101a is configured to actively monitor physiological data, for example, through the use of actuator 109. For instance, as the test user 105 is interacting with VR content 115, when the test user is feeling discomfort and/or sickness, the user may actively engage the actuator 109 (e.g., push a button). The user may also be prompted to input the degree of discomfort/comfort and/or sickness felt during the interaction with VR content 115 at various times (e.g., periodic, random, specified, etc.) through user interface 110.

In another embodiment sensors 125 passively monitor the physiological data while the test user 105 is interacting with VR content 115. That is, sensors 125 automatically monitor and collect the physiological data from the test users. For illustration, physiological data may include electrogastrography, galvanic skin resistance, brain activity (e.g., alpha waves), heart rates, eye movement, head movement, etc. For example an electrogastrogram may show stomach muscle contractions indicative of the onset of nausea. For example, galvanic skin resistance may measure the differences in electrical conductivity or characteristics of the skin. In particular, more sweating will provide better conductivity. It is possible that discomfort and/or sickness caused by certain patterns of VR content 115 (e.g., acrobatic air plane simulation) by the test user 105 may induce a change in the galvanic skin resistance, possibly due to an increase in sweating. Further, brain activity may be measured and recorded over time, to determine if there is some correlation between the measured brain activity and discomfort and/or sickness caused by certain patterns of VR content 115. It is also possible that discomfort and/or sickness may manifest itself in certain eye or head motions, both of which may exhibit slowness or abnormal movement. In addition, the heart rate may exhibit certain patterns when the test users are experiencing discomfort and/or sickness caused by interaction with VR content. Though one item of physiological data, or one type of physiological data may not provide a definitive value in terms of making a correlation between discomfort and/or sickness of a test user and patterns of VR content, over time the certain physiological data or combinations of different types of physiological data collected over many test cases of interactions of test users with VR content will produce more reliable correlations between discomfort and/or sickness and patterns of VR content.

Further, the test data collected in association with the VR content 115 and the physiological data from the test user 105 can be correlated, such that an association can be made between a specific pattern of VR content, or patterns of actions taken by the user in association with the VR content, and physiological reactions, wherein the VR content may induce a measured physiological reaction in the test user 105. For example, a time stamp may be collected in association with both the collected test data associated with the VR content 115 and the physiological data of test user 105, wherein data with corresponding but lagging time stamps may be correlated with each other. In particular, discomfort classification modeler 120 is configured to learn what types and/or patterns of VR content, or patterns associated with the generation of or interaction with VR content, or patterns associated with simulated or tested user interactions with corresponding VR content, is likely to induce discomfort and/or sickness in a user. These identified patterns may be included within a discomfort model 220 that can be used to identify points in an application under test that might induce discomfort and/or sickness in a user.

Figure 1B:
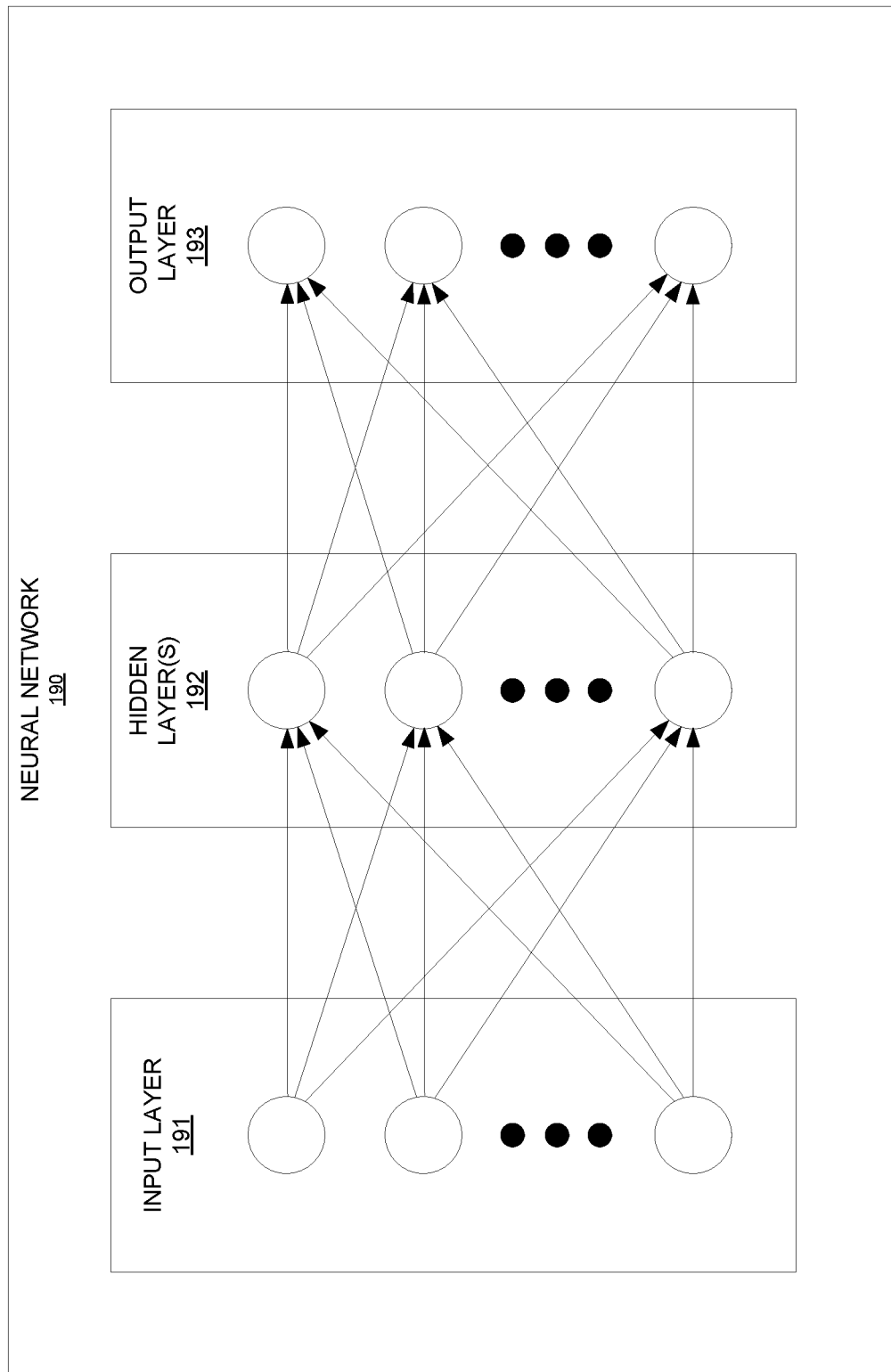
FIG. 1B illustrates an example neural network used to build a discomfort recognition model through training implemented by a deep learning engine, in accordance with one embodiment of the present disclosure.

FIG. 1B illustrates an example neural network used to build a discomfort recognition model through training implemented by the deep learning engine 190 of the discomfort classification modeler 120, in accordance with one embodiment of the present disclosure. In particular, the discomfort classification modeler 120 in system 100A of FIG. 1A is configured to learn what types or patterns of VR content, and/or what actions taken or generated by the user in association with the generation of VR content is likely to induce discomfort and/or sickness in a user (generic, specific, etc.). The discomfort classification modeler 120 may be any computing device, including a back-end server computing device that is coupled to each of the test systems 101a-101n directly or through a network (e.g., local network, internet, etc.).

Specifically, the deep learning engine 190 in the discomfort classification modeler 120 is configured to analyze inputs generated from test users interacting with baseline VR content that has predetermined or true user discomfort and/or sickness responses. As previously described, the inputs include data collected in association with the generation of VR content (e.g., patterns of VR content, and patterns of actions taken or generated by the user in association with the generation of the VR content) and physiological data collected passively by the sensors 125 or actively through the actuator 109. As such, instead of learning why users will react with discomfort and/or sickness when interacting with VR content, the deep learning engine 190 of the discomfort classification modeler 120 is able to recognize which VR content (e.g., types and/or patterns of VR content generated in association with actions taken or generated by the user) when interacted with (e.g., viewing) and/or patterns of actions taken or generated by the user in association with the generation of that VR content, or patterns associated with simulated or tested user interactions with corresponding VR content will cause a user (e.g., generic user, user of a certain type, etc.) to experience discomfort and/or sickness reactions. These patterns are included within a discomfort model 220. In addition, that recognition allows the discomfort classification modeler 120 to build and/or configure the deep learning engine 190 as a content classification model 121. In addition, the discomfort classification modeler 120 is configured to build and/or configure the deep learning engine 190 as a user classification model 122. The models 220, 121 and 122 are related in that they rely on the same recognition of which VR content when interacted will cause a user to experience discomfort and/or sickness reactions.

As previously introduced, associated VR content data (e.g., patterns of VR content, and/or patterns of actions taken or generated by the user in association with the generation of VR content) and physiological data collected passively by the sensors 125 or actively through the actuator 109 are fed to the deep learning engine 190. The deep learning engine 190 utilizes artificial intelligence, including deep learning algorithms, reinforcement learning, or other artificial intelligence-based algorithms. In that manner, during the learning phase, data is collected from test users that interact with baseline VR content, wherein the baseline VR content is associated with predetermined and expected discomfort and/or sickness reactions. Data is also collected from the VR content engine 111 (e.g., patterns of VR content, metadata, patterns of actions taken or generated by the user in association with the generation of VR content etc.). The data is used by the deep learning engine 190 to predict discomfort and/or sickness reactions by users given a set of input data. Analysis on the collected data by the deep learning engine 190 may be continually performed to provide updated analytics used for learning which VR content, patterns of VR content, patterns associated with the generation of or interaction with VR content, or patterns associated with simulated or tested user interactions with corresponding VR content will induce discomfort and/or sickness in users by modifying internal parameters used by the deep learning engine 190. As such, by learning which VR content or patterns of VR content induce discomfort and/or sickness in users, the deep learning engine 190 is able to build models that classify VR content, and classify users during a modeling phase.

The neural network 190 represents an example of an automated analysis tool for analyzing data sets to determine which VR content, patterns of VR content, patterns associated with the generation of or interaction with VR content, or patterns associated with simulated or tested user interactions with corresponding VR content will induce discomfort and/or sickness in users. Different types of neural networks 190 are possible. In an example, the neural network 190 supports deep learning that may be implemented by deep learning engine 190. Accordingly, a deep neural network, a convolutional deep neural network, and/or a recurrent neural network using supervised or unsupervised training can be implemented. In another example, the neural network 190 includes a deep learning network that supports reinforcement learning. For instance, the neural network 190 is set up as a Markov decision process (MDP) that supports a reinforcement learning algorithm.

Generally, the neural network 190 represents a network of interconnected nodes, such as an artificial neural network. Each node learns some information from data. Knowledge can be exchanged between the nodes through the interconnections. Input to the neural network 190 activates a set of nodes. In turn, this set of nodes activates other nodes, thereby propagating knowledge about the input. This activation process is repeated across other nodes until an output is provided.

As illustrated, the neural network 190 includes a hierarchy of nodes. At the lowest hierarchy level, an input layer 191 exists. The input layer 191 includes a set of input nodes. For example, each of these input nodes is mapped to VR content data and physiological data collected passively by the sensors 125 or actively through the actuator 109 collected during interactions of test users with VR content (e.g., video game or gaming application, etc.).

At the highest hierarchical level, an output layer 193 exists. The output layer 193 includes a set of output nodes. An output node represents a decision (e.g., prediction) that relates to one or more components of a user game play profiler, for example. As previously described, the output nodes may identify the state of the test user with reference to discomfort and/or sickness. That is, given a set of inputs the output nodes indicate the level of discomfort and/or sickness state a user is predicted to experience as determined by the deep learning engine 190. These results can be compared to predetermined and true discomfort and/or sickness reactions in order to refine and/or modify the parameters used by the deep learning engine 190 to iteratively determine which VR content or patterns of VR content will induce discomfort and/or sickness in users. That is, the nodes in the neural network 190 learn the parameters of the model that can be used to make such decisions when refining the parameters.

In particular, a hidden layer 192 exists between the input layer 191 and the output layer 193. The hidden layer 192 includes "N" number of hidden layers, where "N" is an integer greater than or equal to one. In turn, each of the hidden layers also includes a set of hidden nodes. The input nodes are interconnected to the hidden nodes. Likewise, the hidden nodes are interconnected to the output nodes, such that the input nodes are not directly interconnected to the output nodes. If multiple hidden layers exist, the input nodes are interconnected to the hidden nodes of the lowest hidden layer. In turn, these hidden nodes are interconnected to the hidden nodes of the next hidden layer, and so on and so forth. The hidden nodes of the next highest hidden layer are interconnected to the output nodes. An interconnection connects two nodes. The interconnection has a numerical weight that can be learned, rendering the neural network 190 adaptive to inputs and capable of learning.

Generally, the hidden layer 192 allows knowledge about the input nodes to be shared among all the tasks corresponding to the output nodes. To do so, a transformation f is applied to the input nodes through the hidden layer 192, in one implementation. In an example, the transformation f is non-linear. Different non-linear transformations f are available including, for instance, a rectifier function $f(x)=\max(0, x)$.

The neural network 190 also uses a cost function c to find an optimal solution. The cost function measures the deviation between the prediction that is output by the neural network 190 defined as f(x), for a given input x and the ground truth or target value y (e.g., the expected result). The optimal solution represents a situation where no solution has a cost lower than the cost of the optimal solution. An example of a cost function is the mean squared error between the prediction and the ground truth, for data where such ground truth labels are available. During the learning process, the neural network 190 can use back-propagation algorithms to employ different optimization methods to learn model parameters (e.g., the weights for the interconnections between nodes in the hidden layers 192) that minimize the cost function. An example of such an optimization method is stochastic gradient descent.

In an example, the training dataset for the neural network 190 is from a same data domain. For instance, the neural network 190 is trained for learning which VR content or patterns of VR content will induce discomfort and/or sickness in users. In this illustration, the data domain includes test session data collected for interactions of test users with baseline VR content. In another example, the training dataset is from different data domains. For instance, the neural network 190 is trained for gaming applications, or for a genre of gaming applications.

As such, the neural network 190 may predict or determine which VR content, patterns of VR content, patterns associated with the generation of or interaction with VR content, or patterns associated with simulated or tested user interactions with corresponding VR content, induces user discomfort and/or sickness. These patterns identified as inducing discomfort and/or sickness are included within a discomfort model 220. Based on these predictive results, the neural network 190 may also define a predictive model (e.g., content classification model 121) that is used to classify VR content based on the predicted user discomfort and/or sickness. Further, the neural network 190 may also define a predictive model (e.g., user classification model) that is used to classify users based on personalized and predicted determinations of user discomfort and/or sickness when viewing VR content.

Figure 2A:
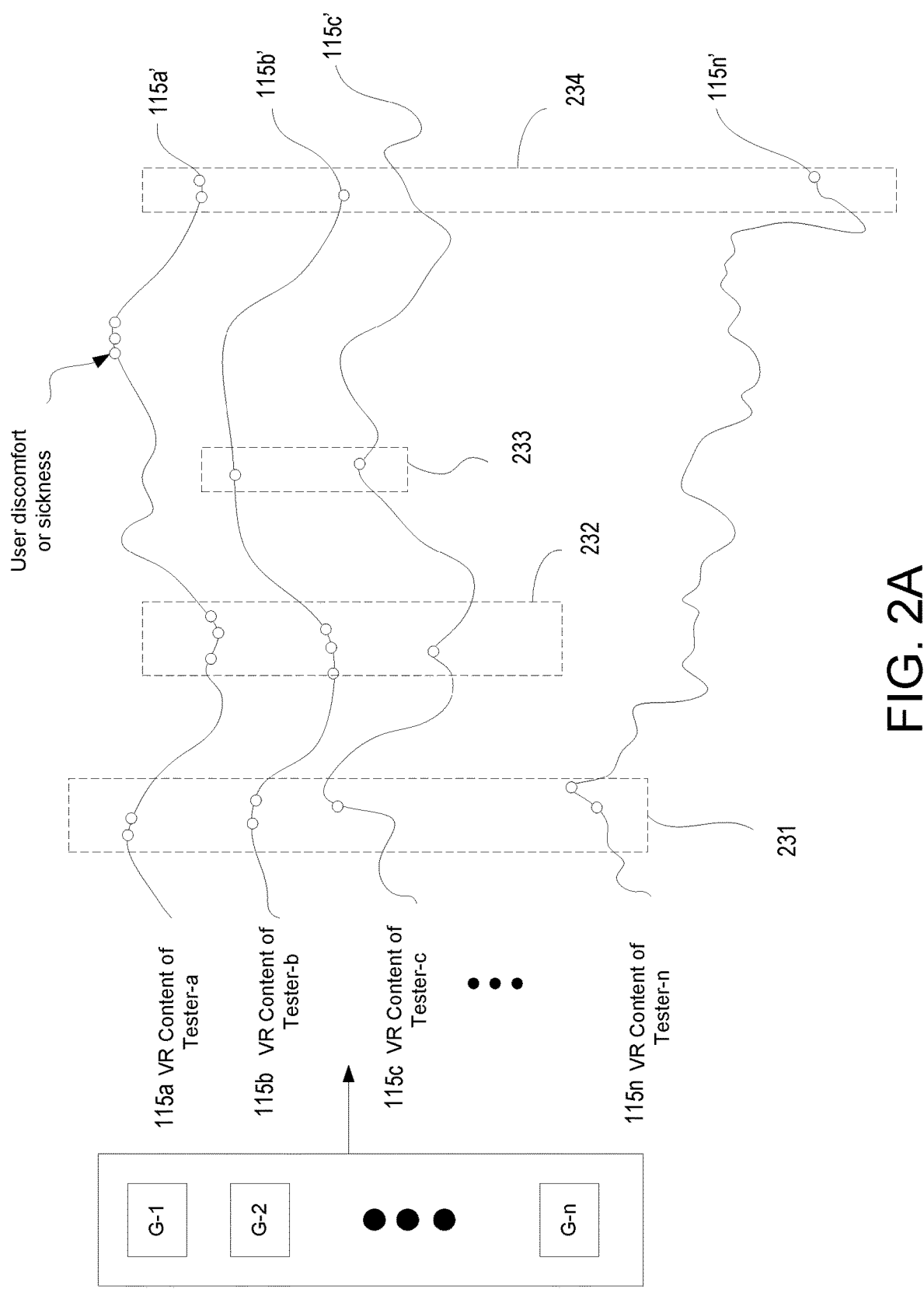
FIG. 2A illustrates the test data that is generated by the system 100A of FIG. 1A, wherein the test data is used for building a discomfort and/or sickness recognition model, in accordance with one embodiment of the present disclosure.

FIG. 2A illustrates the test data that is generated by the system 100A of FIG. 1A, wherein the test data is used for building a discomfort and/or sickness recognition model, in accordance with one embodiment of the present disclosure. As shown, one or more testers (e.g., tester-a through tester-N) interact with one or more test applications (e.g., gaming applications G-1 through G-n). For example, the testers interact with corresponding VR content that is executing on client device 100 using HMD 102. That is, in one embodiment, one application may be used by one or more testers to generate data used for building a discomfort and/or sickness recognition model. In another embodiment, more than one application may be used by one or more testers to generate the data used to build a discomfort and/or sickness recognition model that is configured in part to identify VR content, patterns of VR content, patterns associated with the generation of or interaction with VR content, or patterns associated with simulated or tested user interactions with corresponding VR content, and/or patterns of actions taken or generated by the user in association with the generation of that VR content, that induce discomfort and/or sickness.

As shown, tester-a is interacting with VR content 115a shown by line 115a' that is generated from a corresponding application, such as gaming application G-1. For illustration purposes only, line 115a' is shown as one curved line having peaks and valleys. The path of line 115a' may be analogous to the progress through the gaming application G-1. More importantly, at each point along line 115a' there is associated portions of VR content 115a that is generated and displayed in response to tester-a interaction. Also, at each point, there are associated actions taken or generated by the user in association with the generation of that VR content 115a. In particular, specific zones identified with one or more open circles on the curved line showing portions of VR content 115a correspond to monitored physiological data (passively or actively collected) indicating discomfort and/or sickness in tester-a during his or her interaction with VR content 115a. Snapshots of information may be collected for each zone along line 115a', including associated VR content, metadata, physiological data, actions taken or generated by the user in association with generation of VR content 115a, etc., as previously described. This data may be delivered to the discomfort classification modeler 120 and correlated with other data collected from the other testers to identify or predict patterns of VR content and/or actions taken or generated by the testers in association with generation of or interaction with VR content that induce discomfort and/or sickness.

Similarly, other testers are interacting with other VR content generated by one or more applications G-1 through G-n, and generating data used for identifying or predicting VR content, patterns of VR content, patterns associated with the generation of or interaction with VR content, or patterns associated with simulated or tested user interactions with corresponding VR content, and/or patterns of actions taken or generated by the user in association with the generation of that VR content that induce discomfort and/or sickness. For example, tester-b is interacting with VR content 115b shown by line 115b', tester-c is interacting with VR content 115c shown by line 115c', ... and tester-n is interacting with VR content 115n shown by line 115n'. Data collected in association with each of the VR contents 115a-115n is delivered to the discomfort classification modeler 120, for example. For purposes of illustration, tester-a, tester-b and tester-c may be interacting with VR content generated from one application, such as G-1. This is shown by the similar shapes to curved lines 115a', 115b' and 115c'. In addition, tester-n is interacting with VR content generated from a separate application, such as G-3.

Whether it is one application used for testing, or multiple applications used for testing, the discomfort classification modeler 120 is able to identify or predict VR content, patterns of VR content, patterns associated with the generation of or interaction with VR content, or patterns associated with simulated or tested user interactions with corresponding VR content, and/or patterns of actions taken or generated by the user in association with the generation of that VR content that reliably or are likely to induce discomfort and/or sickness in the testers. For example, highlighted box 231 shows identified zones in VR content 115a, 115b, and 115c that correlate to tester discomfort and sickness. It happens that the zones in box 231 for VR content 115a, 115b, and 115c occur generally at the same progression through the application G-1, as previously introduced. That is, the same patterns of VR content and/or actions taken or generated in association with corresponding VR content are occurring for each of the testers (e.g., tester-a, tester-b, and tester-c). For example, the pattern of VR content may be a FOV having a projected center axis that swings 180 degrees at a high rate, in association with user actions to include running, a double jump, and a quick rotation of head to look down at the landing. Highlighted box 231 includes two points in a zone for VR content 115n that is generated through the execution of a separate application G-3, as previously introduced. These two points are associated with a similar pattern of VR content (e.g., FOV having a projected center axis that swings 180 degrees at a high rate) and/or similar patterns of user actions (e.g., running, a double jump, and a quick rotation of head) though they are generated from application G-3 instead of G-1. Discomfort classification modeler 120 is able to make a correlation between similar VR content, patterns of VR content, patterns associated with the generation of or interaction with VR content, or patterns associated with simulated or tested user interactions with corresponding VR content, and/or patterns of actions taken or generated by the user in association with the generation of that VR content and the induced discomfort and/or sickness in the testers. That is, discomfort classification modeler 120 may identify or predict that the pattern of VR content (FOV having a projected center axis that swings 180 degrees at a high rate) reliably induces discomfort and/or sickness no matter the application source. Also, discomfort classification modeler 120 may identify or predict that the pattern of actions (e.g., running, a double jump, and a quick rotation of head) reliably induces discomfort and/or sickness no matter the application source.

Highlighted box 232 shows identified points of zones in VR content 115a, 115b, and 115c that correlate to tester discomfort and sickness. It happens that these zones in box 232 for VR content 115a, 115b, and 115c occur generally at the same progression through the application G-1, as previously introduced. That is, the same patterns of VR content and/or actions taken or generated in association with corresponding VR content, for example, are occurring for each of the testers (e.g., tester-a, tester-b, and tester-c). Discomfort classification modeler 120 is able to make a correlation between similar VR content, patterns of VR content, patterns associated with the generation of or interaction with VR content, or patterns associated with simulated or tested user interactions with corresponding VR content, and/or patterns of actions taken or generated by the user in association with the generation of that VR content and the induced discomfort and/or sickness in the testers. As such, a common pattern (e.g., a second pattern) of VR content or actions taken or generated in association with corresponding VR content may be classified as inducing discomfort and/or sickness.

Highlighted box 233 shows identified points in zones of VR content 115b and 115c that correlate to tester discomfort and sickness. These points in box 233 occur generally at the same progression through application G-1, as previously introduced. That is, the same patterns of VR content and/or actions taken or generated in association with corresponding VR content are occurring for each of the testers (e.g., tester-b and tester-c). Though tester-a does not show discomfort in this same area in the progression through application G-1 (e.g., tester-a may be immune to this third associated pattern), discomfort classification modeler 120 may still be able to make a correlation between similar VR content, patterns of VR content, patterns associated with the generation of or interaction with VR content, or patterns associated with simulated or tested user interactions with corresponding VR content, and/or patterns of actions taken or generated by the user in association with the generation of that VR content and the induced discomfort and/or sickness in the testers. As such, a common pattern (e.g., a third pattern) of VR content or actions taken or generated in association with corresponding VR content may be classified as inducing discomfort and/or sickness by the discomfort classification modeler 120.

Highlighted box 234 shows identified points in zones of VR content 115a, 115b and 115n that correlate to tester discomfort and sickness. These points in box 234 are based on different applications (e.g., G-1 and G-3), but are grouped according to a similar pattern of VR content and/or actions taken or generated by testers in association with generation of or interaction of corresponding VR content. As such, a common pattern (e.g., a fourth pattern) of VR content, patterns of VR content, patterns associated with the generation of or interaction with VR content, or patterns associated with simulated or tested user interactions with corresponding VR content, and/or patterns of actions taken or generated by the user in association with the generation of that VR content may be classified as inducing discomfort and/or sickness by the discomfort classification modeler 120.

As shown in FIG. 2A, after sufficient test data has been analyzed through a deep learning process, the discomfort classification modeler 120 is able to recognize which VR content, patterns of VR content, patterns associated with the generation of or interaction with VR content, or patterns associated with simulated or tested user interactions with corresponding VR content, and/or patterns of actions taken or generated by the user in association with the generation of that VR content, will induce discomfort and/or sickness. These identified patterns can be included within the discomfort model 220 that can be used to preemptively identify similar patterns in an application under test to understand which zones in that application are predicted to cause a prospective user to experience discomfort and/or sickness.

Figure 2B:
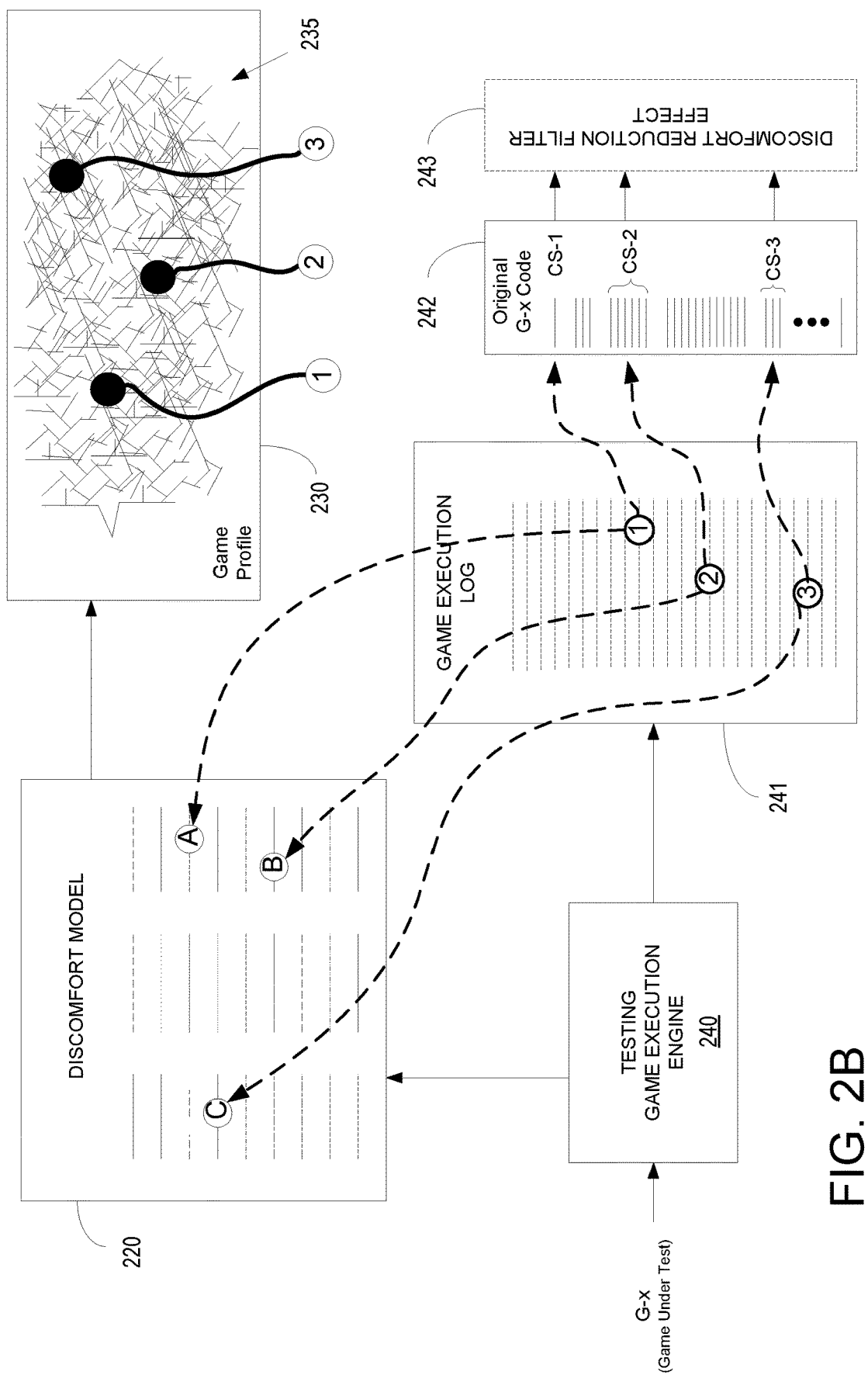
FIG. 2B illustrates the application of a discomfort recognition model to an application under test, wherein the application generates VR content, for purposes of identifying zones or points in the application as executed that are associated with patterns of VR content, and/or patterns of actions taken or generated by the user in association with the generation of that VR content, that induce discomfort and/or sickness, in accordance with one embodiment of the present disclosure.

FIG. 2B illustrates the application of a discomfort model 220 to an application under test (e.g., gaming application, G-x), wherein the application generates VR content, for purposes of identifying points in the application as executed that are associated with VR content, patterns of VR content, patterns associated with the generation of or interaction with VR content, or patterns associated with simulated or tested user interactions with corresponding VR content, and/or patterns of actions taken or generated by the user in association with the generation of that VR content, that induce discomfort and/or sickness, in accordance with one embodiment of the present disclosure. For example, the discomfort model 220 includes one or more items of VR content, patterns of VR content, patterns associated with the generation of or interaction with VR content, or patterns associated with simulated or tested user interactions with corresponding VR content, and/or patterns of actions taken or generated by the user in association with the generation of that VR content that reliably will induce discomfort and/or sickness as determined through testing, as previously described. As shown in FIG. 2B, a plurality of lines is shown, each of which represents a different item of VR content, patterns of VR content, patterns associated with the generation of or interaction with VR content, or patterns associated with simulated or tested user interactions with corresponding VR content, and/or patterns of actions taken or generated by the user in association with the generation of that VR content that is recognized as inducing discomfort and/or sickness in a user.

As shown, the application G-x is executed by the testing game execution engine 140 in order to automatically execute all the various paths and options available in the application. For example, node graph 235 represents all the various paths that can be taken by a user when interacting with application G-x. The testing game execution engine 240 is able to automatically discover and execute all the paths in node graph 235. In addition, as the testing game execution engine 240 executes application G-x, a game execution log 241 is produced that includes information related to the generation of VR content and how the game was executed, such as controller input, metadata, game state data, etc. Further, the information in log 241 may include or be associated with generated VR content, patterns of VR content, patterns associated with the generation of or interaction with VR content, or patterns associated with simulated or tested user interactions with corresponding VR content, and/or patterns of actions taken or generated by the user in association with the generation of that VR content. For example, actions include, in part, run, jump, turn, squat, crawl, speed, trigger gun, turn head, change of view, any kind of movement, pausing, inaction, delay, etc. A pattern of actions may include one or more of these actions.

As the application G-x is executed by testing game execution engine 240, data related to the execution, including data related to the actions taken by user or generated in association with the generation of VR content, such as the information contained in or related to the information contained in game execution log 241, is compared with information in the discomfort model 220 to identify zones in the application G-x that may induce discomfort and/or sickness. For example, zones 1-3 in the game execution log correspond to zones (including points) in the execution of application G-x that each have been identified as being associated with a corresponding VR content, patterns of VR content, patterns associated with the generation of or interaction with VR content, or patterns associated with simulated or tested user interactions with corresponding VR content, and/or patterns of actions taken or generated by the user in association with the generation of that VR content that will induce discomfort and/or sickness. These zones are also identified in the node graph 235. Specifically, point 1 in the execution of application G-x is similar to pattern A in the discomfort model 220, that identifies a corresponding pattern of VR content and/or patterns of actions taken or generated by the user in association with the generation of that VR content, for example, that will induce discomfort and/or sickness. Also point 2 in the execution of application G-x is similar to pattern B in the discomfort model 220 that identifies a corresponding pattern of VR content and/or patterns of actions taken or generated by the user in association with the generation of that VR content, for example, that will induce discomfort and/or sickness. In addition, point 3 determined from the execution of application G-x is similar to pattern C in the discomfort model 220 that identifies a corresponding pattern of VR content and/or patterns of actions taken or generated by the user in association with the generation of that VR content, for example, that will induce discomfort and/or sickness. Each of the patterns A, B and C are unique, and identify different VR content, patterns of VR content, patterns associated with the generation of or interaction with VR content, or patterns associated with simulated or tested user interactions with corresponding VR content, and/or patterns of actions taken or generated by the user in association with the generation of that VR content that will induce discomfort and/or sickness.

Once these zones 1-3 have been identified as being associated with patterns that induce discomfort and/or sickness in users, the corresponding code can also be identified. That is, the zones in the VR content is associated with corresponding code. As shown in FIG. 2B, original G-x code 242 includes sections of code that correspond to various points in the execution of application G-x. For example, zone 1 is associated with code section CS-1 in the original G-x code 242, zone 2 is associated with code section CS-2, and zone 3 is associated with code section CS-3.

After the identification of zones 1-3 based on comparisons to the model 220, the developer may make a decision whether to apply a discomfort reduction filter effect 243 that is configured to reduce any potential discomfort and/or sickness in a user interacting with those zones 1-3. The application of the discomfort reduction filter effect 243 may be imported directly into the code for application G-x, with various options available to the user related to the effect, including enable, disable, magnifying the effect, reducing the magnitude of the effect, etc. For example, the discomfort reduction filter effect 243 may include FOV throttling, which is a reduction in the FOV as the rate of head movement in the virtual world increases, and conversely an increase in the FOV as the rate of head movement decreases. As such, when a view of a user sweeps across a VR environment (e.g., horizon), at the beginning of the sweep the FOV may be around 120 degrees. In the middle of the sweep, when the rate of the head movement may be at its maximum, the FOV may be reduced from 120 degrees down to 80 degrees and even further down to 20 degrees or lower, in a linear or non-linear fashion. Towards the end of the sweep, the rate of head movement again may slow down, and the FOV may be increased from its minimum (e.g., 20 degrees) back up to 120 degrees in a linear or non-linear fashion. A similar throttling can occur for rapid virtual motion relative to proximal objects in the VR simulation.

In one embodiment, the application of the discomfort reduction filter effect 243 may be applied as an overlay to the rendered images generated for display. That is, after the images have been rendered using the application G-x, the discomfort reduction filter effect 243 may then be applied. This post processing may be performed by the application engine, or by the processor of the HMD 102.

Figure 2C:
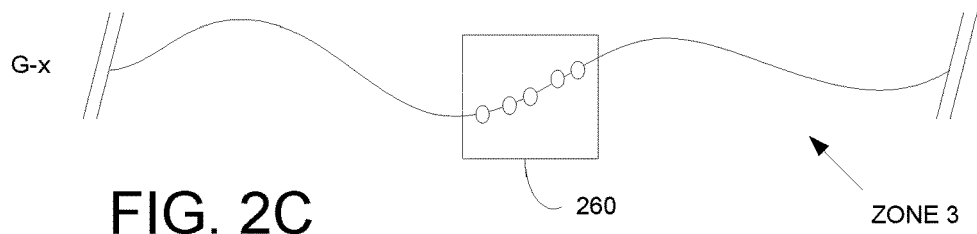
FIG. 2C illustrates the process of identifying zones in VR content that are likely to induce discomfort and/or sickness based on predicted discomfort of a user as determined by a model configured for predicting discomfort of a user when interacting with VR content, in accordance with one embodiment of the present disclosure.

FIG. 2C illustrates identified zones in VR content that are likely to induce discomfort and/or sickness based on predicted discomfort of a user as determined by a model configured for predicting discomfort of a user when interacting with VR content, in accordance with one embodiment of the present disclosure. In particular, zone 3 of application G-x is highlighted in FIG. 2C, wherein zone 3 was previously introduced in FIG. 2B. As shown, zone 3 includes a pattern of actions 260 taken or generated in association with the generation of corresponding VR content that will likely induce discomfort and/or sickness. For example, 5 actions are shown in zone 3, and may include a sequence of actions related to crawling through a culvert at night, wherein a flashlight illuminates the culvert in a sporadic, uneven manner, and possibly frantic manner, and where a mass of crickets is jumping around the user. The user may be taking actions to include crawling, turning the head in response to crickets hitting the user or coming into the view of the user such that that user is turning the head to avoid the jumping crickets, making a rolling action to get around a blocking object, and quickly scanning around the culvert. These actions are provided for illustration only.

Figure 3A:
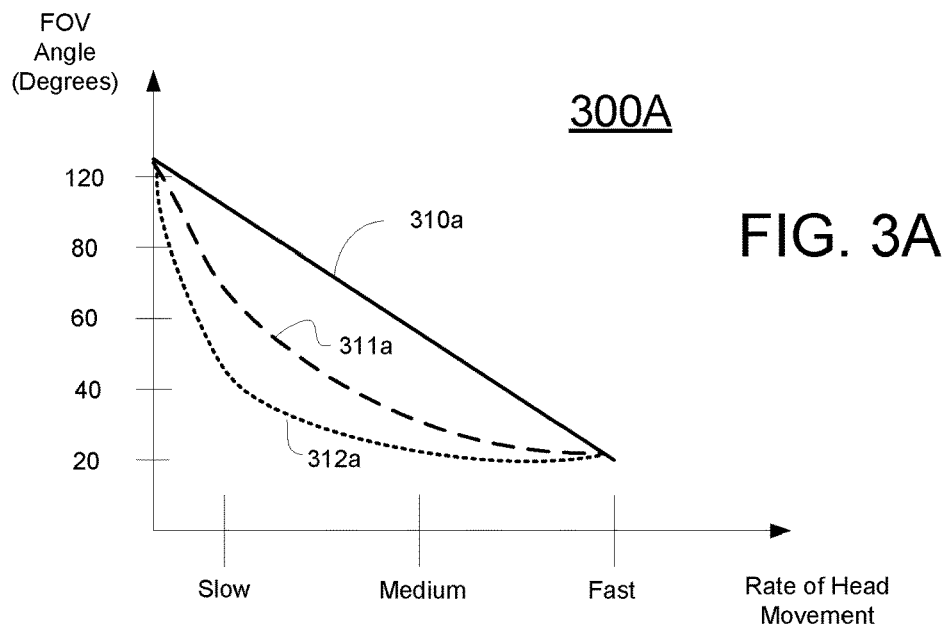
FIG. 3A is a graph illustrating the application of a discomfort reduction filtering effect in zones in VR content that are predicted to induce discomfort and/or sickness as determined by a model configured for predicting discomfort of a user when interacting with VR content, including implementation of field of view (FOY) throttling in proportion to the rate of head movement of a user, in accordance with one embodiment of the present disclosure.

FIG. 3A is a graph 300A illustrating the application of a discomfort reduction filtering effect in zones identified in VR content that are predicted to induce discomfort and/or sickness as determined by a model configured for predicting discomfort of a user when interacting with VR content, including implementation of field of view (FOY) throttling in proportion to the rate of head movement of a user, in accordance with one embodiment of the present disclosure. As shown, graph 300A includes an x-axis that shows the rate of head movement, wherein the rate increases from a static position at the origin to a slow rate, to a medium rate, and to a fast rate as the value of x increases. Along the y-axis, graph 300A shows the FOV rendered for a given rate of head movement.

Generally, the FOV of a VR environment as shown to a user is reduced as the rate of head movement increases. The reduction may be linearly applied, or non-linearly applied. The values for FOV are chosen for illustrative purposes, and may include a FOV between 0 and 360 degrees in embodiments. For example, line 310a shows a linear reduction in the FOV from 120 degrees down to 20 degrees as the rate of head movement increases. Similarly, line 310a shows a linear increase in the FOV from 20 degrees to 120 degrees as the rate of head movement decreases. The head movement may be illustrative of a sweep of the horizon from a static position, increased head movement to a maximum rate of movement, and decreased head movement back to a static position, wherein the sweep is performed mostly at a constant rate. A similar approach can be used for other head movement such as rapid movement in a virtual world relative to proximal virtual objects.

In addition, line 311a shows a non-linear reduction in the FOV from 120 degrees down to 20 degrees as the rate of head movement increases. The reduction in the beginning is more drastic than in line 310a. Similarly, line 311a shows a non-linear increase in the FOV from 20 degrees up to 120 degrees as the rate of head movement decreases. As such, as soon as head movement is detected, FOV throttling is immediately applied, with more magnitude than line 310a exhibiting a linear application. That is, the magnitude of the reduction of FOV for line 311a is greater than for line 310a, wherein even at a slow rate of head movement, FOV may be throttled by fifty percent from 120 degrees down to approximately 60 degrees.

Also, line 312a shows a non-linear reduction in the FOV from 120 degrees down to 20 degrees as the rate of head movement increases. The reduction in the beginning is more drastic than in line 311a. Further, line 312a shows a non-linear increase in the FOV from 20 degrees up to 120 degrees as the rate of head movement decreases. That is, FOV throttling is applied with even more magnitude in line 312a than in line 311a. For example, at the slow rate of head movement, FOV may be throttled by approximately 60-70 percent from 120 degrees down to approximately 40 degrees or lower.

Figure 3B:
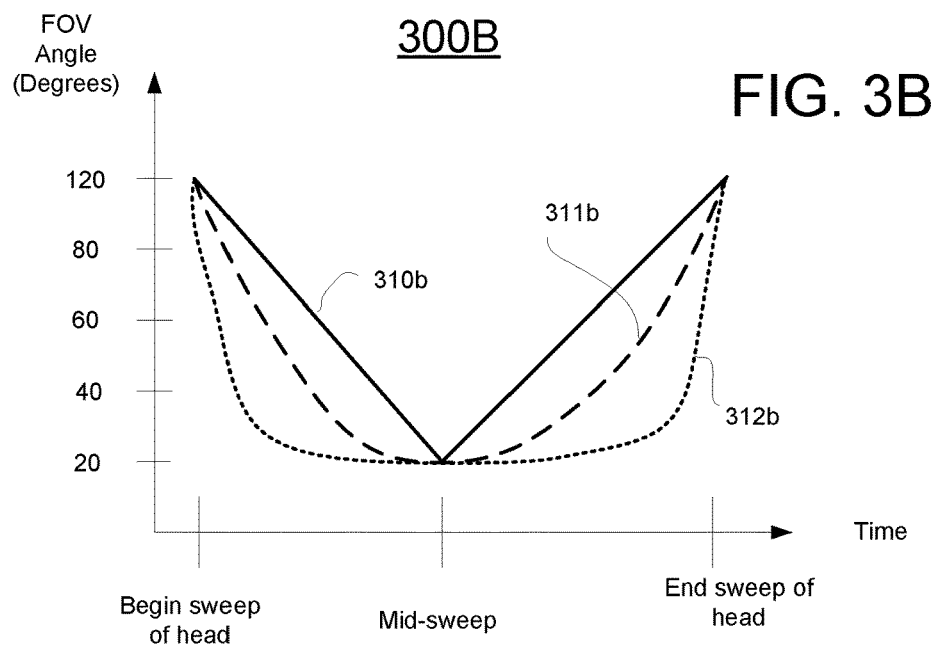
FIG. 3B is a graph illustrating the application of a discomfort reduction filtering effect in zones in VR content that are predicted to induce discomfort and/or sickness as determined by a model configured for predicting discomfort of a user when interacting with VR content, including implementation of FOV throttling as the head of a user is moving in time, in accordance with one embodiment of the present disclosure.

FIG. 3B is a graph 300B illustrating the application of a discomfort reduction filtering effect in zones of VR content and/or the source of VR content that are predicted to induce discomfort and/or sickness as determined by a model configured for predicting discomfort of a user when interacting with VR content, including implementation of FOV throttling as the head of a user is moving in time, in accordance with one embodiment of the present disclosure. An effect implementing FOV throttling includes a reduction in the FOV as the rate of head movement increases, and conversely an increase in the FOV as the rate of head movement decreases. In particular, graph 300B includes an x-axis that shows time, and a y-axis that shows the FOV rendered for a given time. As an example of head movement, the user may be sweeping from left to right, or right to left, across a horizon over time. In addition, the head may be moving up or down, or in any random direction or directions. The sweep begins from a static position, may be related to an increase in the rate of movement to a maximum, and may be related to a decrease in the rate of head movement back to a static position.

FIG. 3B is related to FIG. 3A, as it provides an example of the application of FOV throttling introduced in FIG. 3A. In particular, for the linear reduction and increase of FOV throttling in response to a rate of head movement as described in line 310a of FIG. 3A, line 310b of FIG. 3B shows how the FOV changes over time. For example, at the beginning of the sweep, the FOV is at 120 degrees, and as the user sweeps to a mid-sweep position, the FOV is linearly reduced down to 20 degrees. Further, as the user sweeps from the mid-sweep position to an end of the sweep to a desired viewpoint, the FOV is linearly increased from 20 degrees up to 120 degrees.

In particular, for the non-linear reduction and increase of FOV throttling in response to a rate of head movement as described in line 311a of FIG. 3A, line 312b of FIG. 3B shows how the FOV changes over time. For example, at the beginning of the sweep, the FOV is at 120 degrees, and as the user sweeps to a mid-sweep position, the FOV is non-linearly reduced down to 20 degrees. Further, as the user sweeps from the mid-sweep position to an end of the sweep to a desired viewpoint, the FOV is non-linearly increased from 20 degrees up to 120 degrees. As shown in line 310b, the rate of FOV change is constant over time on either side of the mid-sweep point.

Also, for the non-linear reduction and increase of FOV throttling in response to a rate of head movement as described in line 312a of FIG. 3A, line 312b of FIG. 3B shows how the FOV changes over time. For example, at the beginning of the sweep, the FOV is at 120 degrees, and as the user sweeps to a mid-sweep position, the FOV is non-linearly reduced down to 20 degrees. Further, as the user sweeps from the mid-sweep position to an end of the sweep to a desired viewpoint, the FOV is non-linearly increased from 20 degrees up to 120 degrees. That is for lines 311b and 312b, the effect of FOV throttling is shown with increasing levels of magnitude.

Figure 3C:
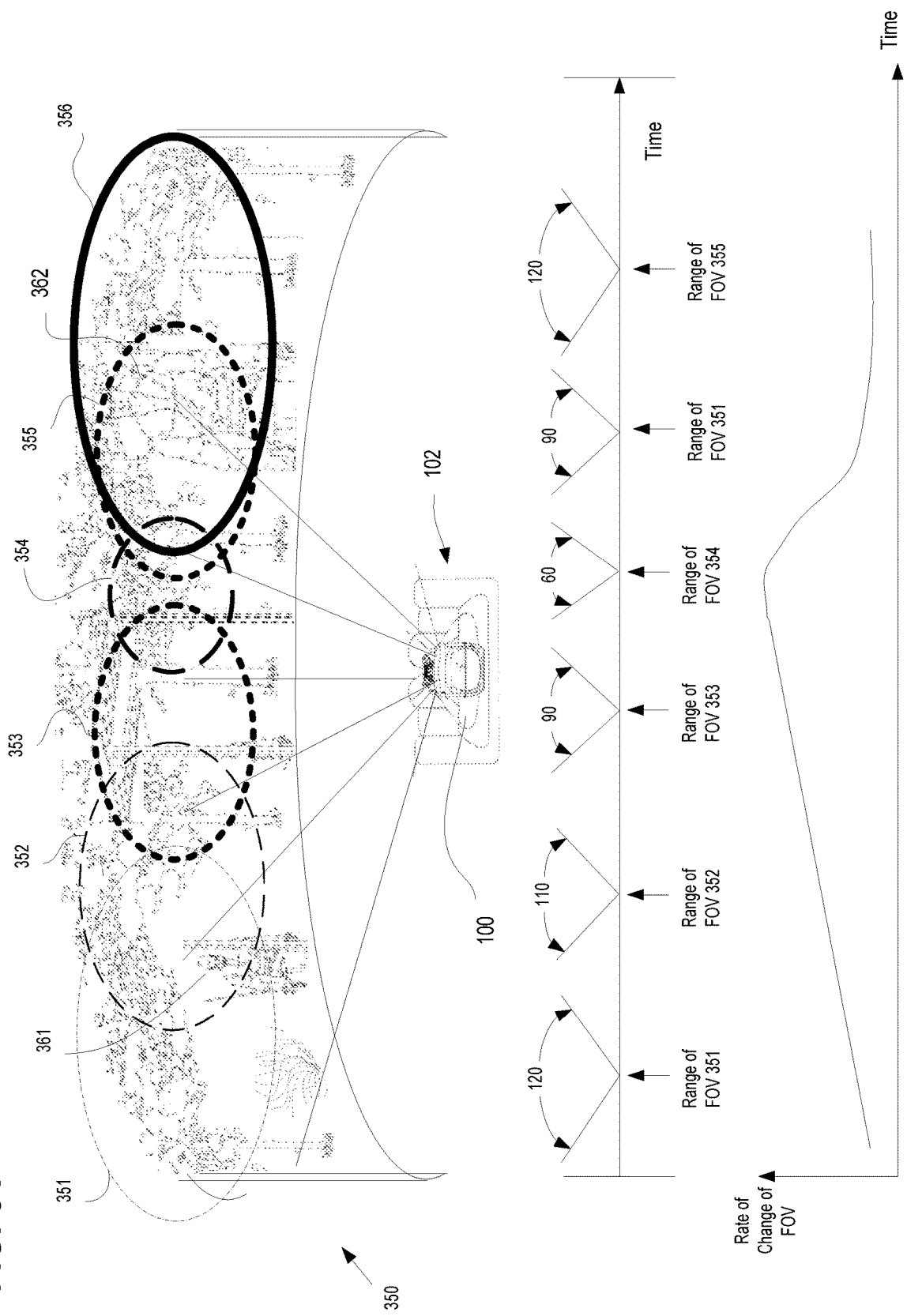
FIG. 3C is an illustration of an VR environment and the application of FOV throttling within the view of a user as the head of a user is physically moving, in accordance with one embodiment of the present disclosure.

FIG. 3C is an illustration of a VR environment 350 and the application of FOV throttling within the view of a user 100 through an HMD 102, as the head of a user is physically sweeping through the VR environment 350 from left to right, in accordance with one embodiment of the present disclosure. At the beginning of the sweep, the user is viewing a soldier 361 in a FOV 351 that may encompass 120 degrees, for example, as shown in the middle graph. As the user 100 sweeps to the right, the FOV will be reduced. For example, FOV 352 may encompass 110 degrees. As the sweeps further to the right, FOV 353 may encompass 90 degrees. Sweeping even further to the right, FOV 354 is at its smallest at approximately 60 degrees. The rate of change of the sweeping motion (e.g., head movement) may be linear between FOV 351 to FOV 354, as shown by the bottom graph. In addition, the FOV may shrink in overall size also as FOV 351 both has a larger range (e.g., 120 degrees) and also a larger height, than FOV 354, which has the min range (e.g., 60 degrees) and the smallest height, in one embodiment.

After the point associated with FOV 354 during the head sweep, the rate of head movement may non-linearly decrease until the user reaches the desired view represented by FOV 356. For example, the user may quickly slow down the rate of head movement between FOV 354 and FOV 355. This is shown in the bottom graph as a quick reduction in the rate of change of FOV, where the head movement may be slowing down quickly. For example, FOV 354 may be increased to 90 degrees at FOV 355. Sweeping further to the right, at the end of the sweep, FOV 356 is increased back to 120 degrees. At this point, the FOV remains at 120 degrees as there is no further head movement, and the rate of change is near zero.

In addition, FIG. 3C shows the application of the discomfort reduction filtering effect as a narrowing of the width and height of FOV generally as an ellipsoid. However, other FOV shape applications are contemplated, such that the FOV may take on one or more shapes, such as an ellipse, or circle, or box, or rectangle. Further, the FOV may have rounded, or blurred edges for purposes of softening the discomfort reduction filtering effect. The shape may also be asymmetric in proportion to proximity of objects in the virtual space and the direction of head movement.

Further, a foveated view within the FOV of FIG. 3C may be adjusted to apply a discomfort reduction filtering effect. In particular, the foveated view may include one or more clarity regions centered about a corresponding point of clarity, each clarity region having the highest amount of resolution across the image shown in a corresponding FOV. In the foveated view, regions outside the one or more clarity regions may have decreased resolution (e.g., more blurry). For example, as the discomfort level is increasing (e.g., as the user is moving his head) a clarity region may change shape, such as decreasing the size of the clarity region (e.g., decreasing the size of an ellipsoid clarity region). As such, while the FOV remains the same, a clarity region may decrease in size in the corresponding FOV, in one embodiment. In other embodiment, while the FOV is shrinking to apply a discomfort reduction filtering effect, the foveated view may also be changed (e.g., decrease in size), in one embodiment. As the discomfort level is decreasing, the foveated view may then revert back to its original state (e.g., increasing the clarity region while the FOV remains constant, increasing the clarity region while also increasing the FOV, etc.).

In still another embodiment, eye tracking may be combined with display of a foveated view. In particular, eye tracking is performed to track the direction of view for each eye. In addition, the shape of the eye is tracked, wherein the shape includes shape of pupil, cornea, iris, body, etc. For example, various components of the eye may change shape depending on how the eye is being used. Based on the tracking, a 3D image of a corresponding eye may be generated, wherein the 3D image includes the shape and direction of the eye. With regards the foveated view, a clarity region may be modified depending on the characteristics (e.g., shape and/or direction) of a corresponding eye. That is, as a corresponding eye moves, the foveated view for that eye within a FOV may also move. For some users, by tracking both eyes separately, the foveated view for a lazy eye may be different than a foveated view for a dominant eye. Combining both foveated views in the HMD would result in a better 3D image (e.g., increased clarity and resolution). In addition, as the discomfort level of the user increases, the foveated view may be changed, as previously described. Further, the discomfort level may be determined based on the eye tracking. For example, as the pupil changes shape (rate and type of shape), this may indicate a degree of discomfort, which may be translated to a modification of the foveated view. In addition, the position of clarity regions within the foveated view may be predicted depending on the circumstances. Eye tracking may provide some indication where the eye is moving, with a corresponding prediction of a corresponding foveated view. In addition, the game environment may dictate where the user will direct his gaze. For example, if within the game play of a user, when the game environment is in a state where a known event will occur prompting the user to direct eye gaze in the direction of the event, then a foveated view in that direction could be predicted. In that case, the foveated view may be generated earlier even before the eye of the user is directed in the direction of the event. Other predictive applications are also envisioned.

Figure 3D:
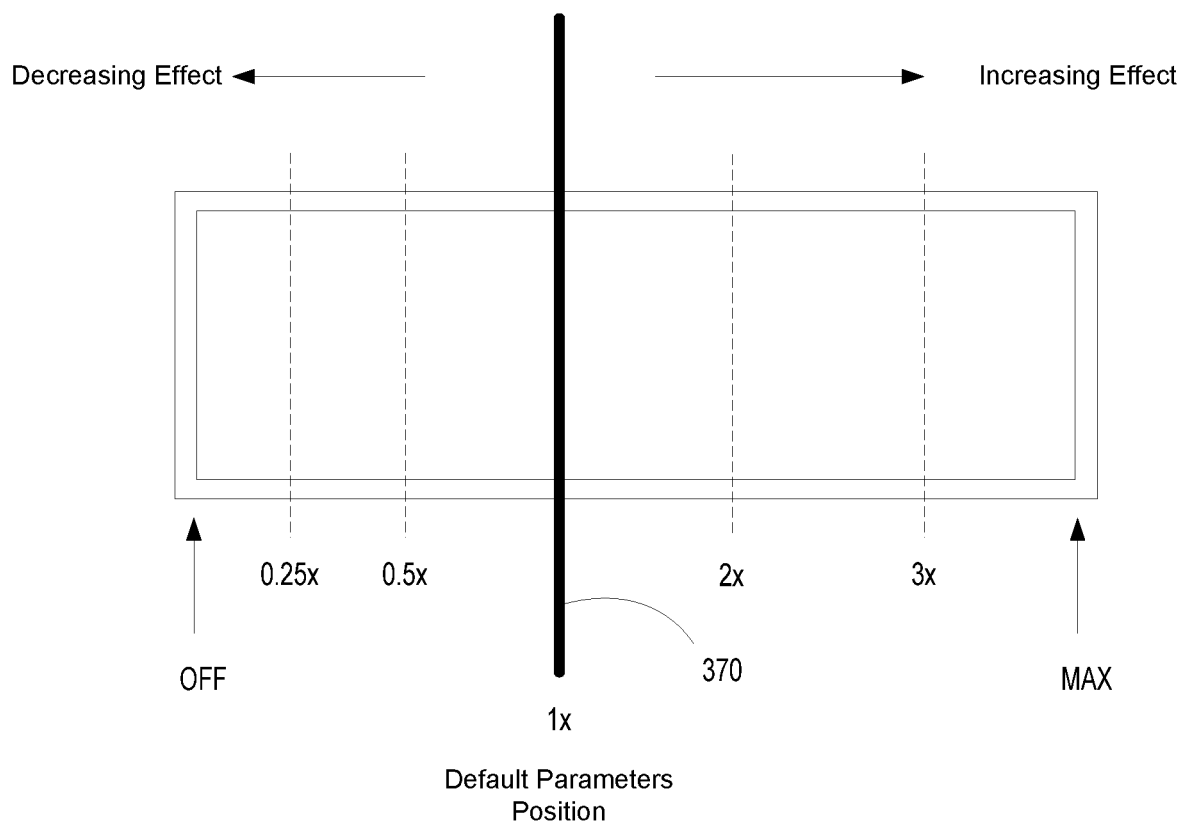
FIG. 3D is an illustration of a slider bar configured to adjust the application of a discomfort reduction filtering effect in zones in VR content that are predicted to induce discomfort and/or sickness as determined by a model configured for predicting discomfort of a user when interacting with VR content, in accordance with one embodiment of the present disclosure.

FIG. 3D is an illustration of a slider bar 370 that is configured to adjust the application of a discomfort reduction filtering effect (e.g., FOV throttling) in zones of VR content that are predicted to induce discomfort and/or sickness as determined by a model configured for predicting discomfort of a user when interacting with VR content, in accordance with one embodiment of the present disclosure.

In one embodiment, the discomfort reduction filtering effect is applied to identified zones in VR content, as previously described. That is, the discomfort reduction filtering effect is applied during processing of the application, such as when rendering images. The discomfort reduction filtering effect is associated with default parameters that define how the discomfort reduction filtering effect is applied. For example, as shown in FIG. 3D, the slider bar is positioned in a default position (e.g., the center of the slider bar) within a range between an OFF position for the discomfort reduction filtering effect and a MAX position signifying a maximum discomfort reduction filtering effect.

The slider bar 370 allows the user to adjust the default parameters. In particular, as the slider bar 370 is moved to right, the parameters are changed so that the discomfort reduction filtering effect has an increased effect. For example, the magnitude of the effect may be increased (e.g., instead of 1× default implementation of the discomfort reduction filtering effect, it may be increased to 2× or 3×). This may result in a more aggressive reduction of the FOV, for example from 120 to 20 degrees (e.g., as shown by lines 311a and 311b, or 312a and 312b). In addition, the amount of reduction may be managed. For example, as the slider bar is moved to the right, the FOV may be reduced down further than 20 degrees at its minimum value.

On the other hand, as the slider bar 370 is moved to the left, the parameters are changed so that the discomfort reduction filtering effect has a reduced effect. By moving all the way to the left, the discomfort reduction filtering effect may be disabled. For example, the magnitude of the effect may be decreased. (e.g., instead of a 1× default implementation of the discomfort reduction filtering effect, it may be decreased to 0.5×, or 0.25×). This may result in a less aggressive reduction of the FOV when moving from 120 to 20 degrees. For example, the reduction may occur very slowly (e.g., as shown by lines 310a and 310b with a linear application). In addition, the amount of reduction may be managed. For example, as the slider bar is moved to the left, the FOV may be increased at its minimum value, such that instead of 20 degrees, the minimum FOV may be 45 degrees.

In another embodiment, the slider bar 370 is enabled by the user for purposes of applying in real-time a discomfort reduction filtering effect (e.g., FOV throttling) as an overlay to VR content generated in association with execution of the first application. That is, the user is able to apply discomfort reduction filtering effect at any point during his or her interaction with the VR content. In this way, the user does not have to rely on the developer to provide discomfort reduction filtering effect at selective zones in the VR content. The user may be extremely prone to exhibit or experience discomfort and/or sickness when viewing any VR content. As such, the user is able to enable an overlay feature that allows the application of the discomfort reduction filtering effect to any VR content (e.g., previously rendered images ready for display), as previously described. The user is given various control options, including enabling or disabling the discomfort reduction filtering effect, controlling the application (e.g., magnitude of the effect) of the discomfort reduction filtering effect (e.g., through a slider bar described above), etc. In this manner, when the user begins to feel discomfort during interaction with VR content, the user is able to enable the discomfort reduction filtering effect (e.g., FOV throttling) and control its application to the VR content through an overlay process when presenting the VR content.

Figure 4A:
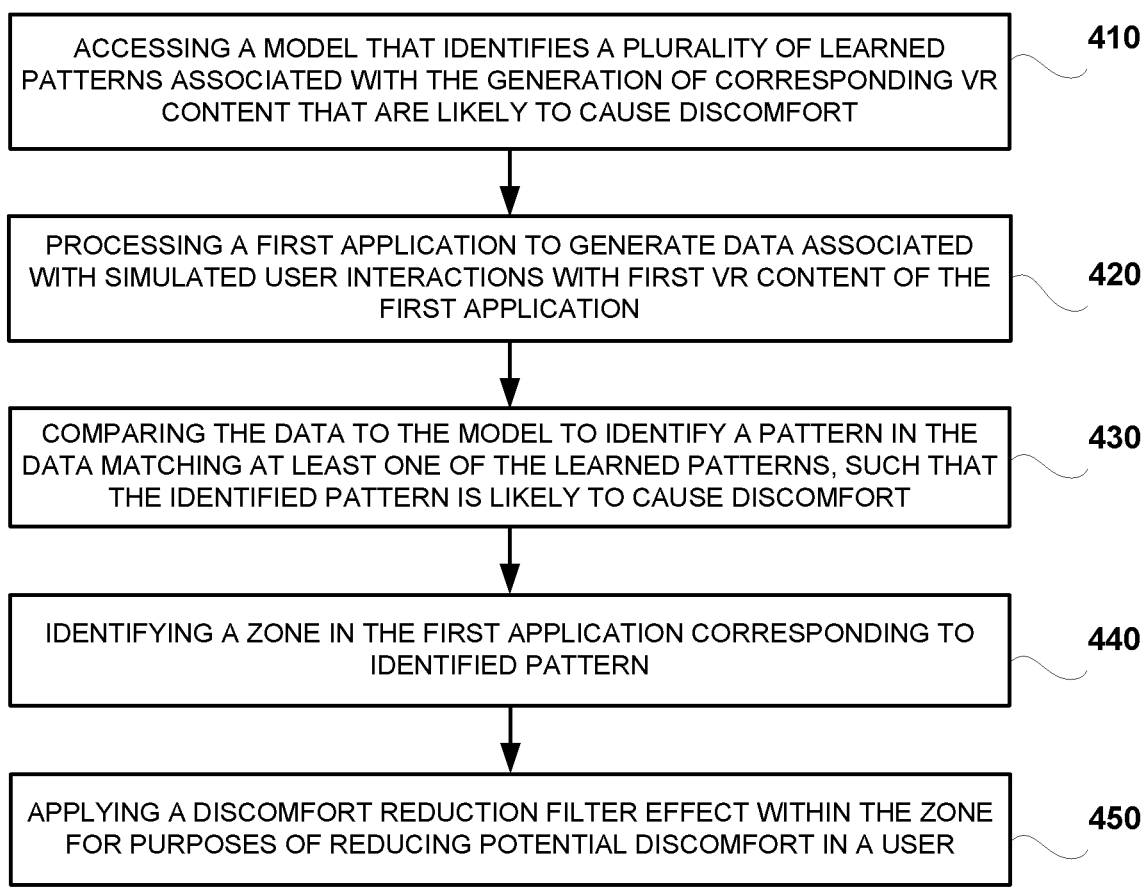
FIG. 4A is a method for applying of a discomfort reduction filtering effect in zones in VR content that are predicted to induce discomfort and/or sickness as determined by a model configured for predicting discomfort of a user when interacting with VR content, including implementation of FOV throttling as the head of a user is moving in time, in accordance with one embodiment of the present disclosure.

With the detailed description of the various modules of a VR content classification system, a method for classifying VR content based on predicted levels of discomfort and/or sickness induced by that VR content is now described in relation to flow diagram 400A of FIG. 4A, in accordance with one embodiment of the present disclosure. The method outlined in flow diagram 400A is implemented by the systems and/or components of FIGS. 1A-1B, 2A-2C, and 3A-3D, in embodiments. In particular, FIG. 4A is a method for applying of a discomfort reduction filtering effect in zones in VR content that are predicted to induce discomfort and/or sickness as determined by a model configured for predicting discomfort of a user when interacting with VR content, including implementation of FOV throttling as the head of a user is moving in time, in accordance with one embodiment of the present disclosure.

At operation 410, the method includes accessing a model that identifies a plurality of learned patterns associated with the generation of corresponding VR content that are likely to cause discomfort. The generated model also predicts a level of discomfort experienced by a participating user when interacting with corresponding virtual reality (VR) content. For example, content classification model 121 may be generated at operation 310, and is based on the discomfort model 220 generated by modeler 120 that has learned to recognize which VR content (e.g., types and/or patterns of VR content) when interacted with (e.g., viewing) will cause to user 105 to experience discomfort and/or sickness reactions. Learned patterns include VR content, patterns of VR content, patterns associated with the generation of or interaction with VR content, or patterns associated with simulated or tested user interactions with corresponding VR content, and/or patterns of actions taken or generated by the user in association with the generation of that VR content that are likely to cause discomfort and/or sickness.

In particular, a deep learning engine may be configured to receive physiological data from test users during their interactions with baseline VR content, as previously described. The deep learning engine analyzes baseline VR content data and physiological data collected passively or actively from test users to learn which VR content (e.g., types, patterns, etc.) when interacted with will cause a user to experience discomfort and/or sickness reactions. As such, over time, input data related to VR content and physiological reactions to VR baseline content can be aligned with known and expected reactions to the VR baseline content. In that manner, certain VR content, patterns of VR content, patterns associated with the generation of or interaction with VR content, or patterns associated with simulated or tested user interactions with corresponding VR content, and/or patterns of actions taken or generated by the user in association with the generation of that VR content may be recognized as inducing discomfort and/or sickness in test users, and applied to classify VR content or users based on predicted discomfort and/or sickness induced or experienced by users.

At operation 420, the method includes processing a first application to generate data associated with simulated user interactions with first VR content of the first application. The processing operation may include execution of the first application to generate first VR content. For example, the first application is executed by the testing game execution engine 240 of FIG. 2B to simulate user interaction with all the various paths available in the first application. The processing operation may include extracting data associated with simulated user interactions with the first VR content generated during execution of the first application. This extracted data is applied to the model. The extracted data includes characteristics of the first VR content generated during the simulation of user interaction with the first VR content. The data may include VR content, patterns of VR content, patterns associated with the generation of or interaction with VR content, or patterns associated with simulated or tested user interactions with corresponding VR content, and/or patterns of actions taken or generated by the user in association with the generation of that VR content. Further, the data may include in-content features including executable code, at least one static image, a sequence of static images, video, audio, etc. For example, various segments of the VR content may be randomly selected, or segments at periodic intervals may be selected. In addition, particular types of images, scenes, and/or sequence of images or scenes may be identified and used as in-content features. This data is used to classify the first VR content in terms of identifying points or zones in the VR content or first application (e.g., source of the first VR content) that are likely to cause discomfort and/or sickness.

At operation 430, the method includes comparing the extracted data to the model to identify one or more patterns (e.g., a pattern) in the extracted data matching at least one of the learned patterns from the model such that the one or more patterns are likely to cause discomfort. For example, VR content, patterns of VR content, patterns associated with the generation of or interaction with VR content, or patterns associated with simulated or tested user interactions with corresponding VR content, and/or patterns of actions taken or generated by the user in association with the generation of that VR content, that match the learned patterns can also be determined to likely cause discomfort and/or sickness.

At operation 440, the operation includes identifying a zone in the first application corresponding to the identified pattern. The zone in the first application (e.g., code) may be associated with the matched VR content, patterns of VR content, patterns associated with the generation of or interaction with VR content, or patterns associated with simulated or tested user interactions with corresponding VR content, and/or patterns of actions taken or generated by the user in association with the generation of that VR content. Once the first application is classified, further actions may be performed.

For example, at operation 450, the method includes applying a discomfort reduction filter effect within the zone for purposes of reducing potential discomfort in a user. In one embodiment, the method includes applying field of view throttling to VR content generated in association with execution of the first application in the zone. The FOV throttling may be included within the first application, especially after the zone has been identified during the design phase, in one embodiment. In another embodiment, the FOV throttling may be applied in real-time as an overlay to VR content generated in association with execution of the first application, such as after the images have been rendered by the first application, wherein the FOV throttling is applied as an overlay to the images to be displayed on the HMD. For example, FOV throttling may include decreasing a field of view as the rate of head movement of the user increases, and/or increasing a field of view as the rate of head movement of the user decreases.

In one embodiment, a user interface is presented that allows the user to change parameters in the discomfort reduction filter effect. For example, the user interface may be a slider, as previously described in FIG. 3D. The slider allows for the user to change parameters affecting the implementation of the discomfort reduction filter effect, such as FOV throttling. In one embodiment, the magnitude of the discomfort reduction filter effect is increased in response to a change in parameters. In another embodiment, the magnitude of the discomfort reduction filter effect is decreased in response to a change in parameters. Further, the user interface may allow for other control, such as disabling the discomfort reduction filter effect in response to a request from the user, or enabling the discomfort reduction filter effect in response to a request from the user.

In one embodiment, a method is disclosed for applying a discomfort reduction filtering effect in zones in VR content that are predicted to induce discomfort and/or sickness as determined by a model configured for predicting discomfort of a user when interacting with VR content, including implementation of FOV throttling as the head of a user is moving in time, in accordance with one embodiment of the present disclosure. The method includes executing an application to generate VR content for interaction by a user. The method includes receiving an input indicating discomfort in the user. The method includes applying a discomfort reduction filter effect to VR content currently displayed purposes of reducing potential discomfort, such as applying FOV throttling to the VR content generated for display. For example, FOV throttling may be applied as an overlay to the rendered VR content that is generated for display.

In one embodiment, the input is generated actively by the user. For example, the user may engage an actuator to indicate discomfort, and the request to implement a discomfort reduction filtering effect. In that manner, the physiological data may be actively monitored, such as when a user activates an actuator (e.g., button) indicating when the user is experiencing discomfort and/or sickness.

In another embodiment, the input is generated passively by the user. For example, the physiological responses of the user may be monitored while the user is interacting with the content. Physiological measurements may be passively monitored. For example, physiological data may include electrogastrography, galvanic skin resistance, brain activity (e.g., alpha waves), heart rates, eye movement, eye gaze, head movement or motion, etc. These measurements may be correlated with in-content features, as will be described below. In addition, known patterns of physiological measurements are associated with expected discomfort reactions. For example, a correlation may be made between increased galvanic skin resistance (e.g., indicating more sweating) and increased discomfort. Though a direct correlation may not be proven between any one measurement, the method of flow diagram 400 is able to learn and/or recognize which VR content (e.g., types, patterns, combinations of patterns, etc.) when interacted with will cause a user to experience discomfort and/or sickness reactions. For example, VR content, patterns of VR content, patterns associated with the generation of or interaction with VR content, or patterns associated with simulated or tested user interactions with corresponding VR content, and/or patterns of actions taken or generated by the user in association with the generation of that VR content may be identified as causing a user to experience discomfort and/or sickness reactions.

In one embodiment, the discomfort reduction filter effect is applied to VR content as an overlay process performed on the VR content, as previously described. For example, FOV throttling may be applied in real-time as an overlay to the VR content to be displayed.

Figure 4B:
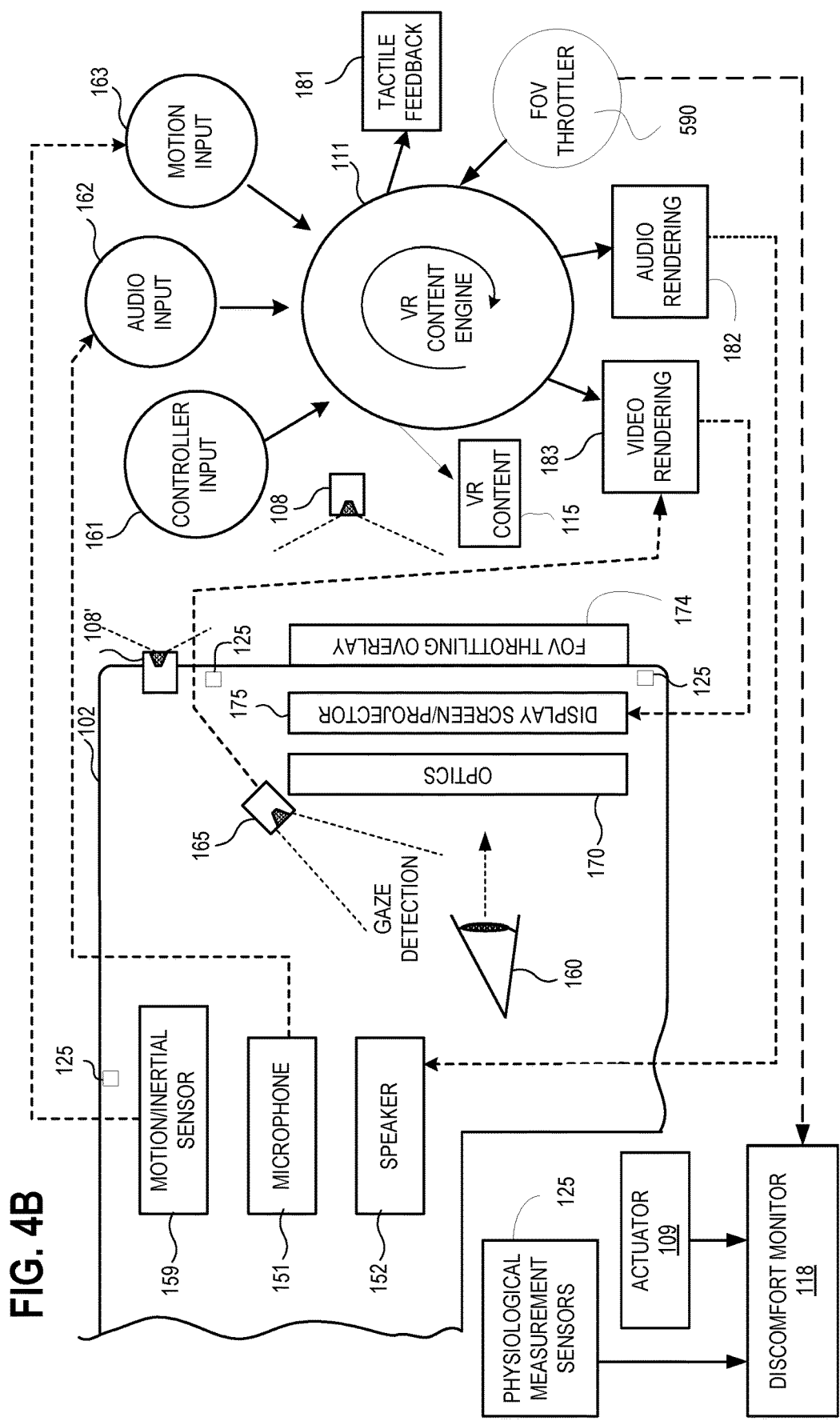
FIG. 4B conceptually illustrates the function of a HMD in conjunction with the execution of an application generating VR content and the application of a discomfort reduction filtering effect in a closed loop system, in accordance with an embodiment of the invention.

FIG. 4B conceptually illustrates the function of a HMD in conjunction with the execution of an application (e.g., execution of an application and/or video game, etc.) generating VR content and the application of a discomfort reduction filtering effect in a closed loop system, in accordance with an embodiment of the invention. That is, the discomfort reduction filtering effect may be automatically applied in response to indications that the user is experiencing discomfort, in accordance with one embodiment of the present disclosure. In some implementations, the VR content engine 111 is being executed on a client device 100 (not shown) that is communicatively coupled to the HMD 102, as previously described. For example, the VR content engine 111 executing an application may be a gaming engine executing a video game, and is configured to receive inputs to update a game state of the video game. The gaming engine may be a gaming console, or back-end gaming server, as previously described. The game state of the video game can be defined, at least in part, by values of various parameters of the video game which define various aspects of the current gameplay, such as the presence and location of objects, the conditions of a virtual environment, the triggering of events, user profiles, view perspectives, actions taken by the user 105, controller actions, gaze tracking information, etc.

In the illustrated embodiment, the VR content engine 111 receives, by way of example, controller input 161, audio input 162 and motion input 163. The controller input 161 may be defined from the operation of a gaming controller separate from the HMD 102, such as a hand-held gaming controller 104 (e.g. Sony DUALSHOCK®4 wireless controller, Sony PlayStation® Move motion controller) or wearable controllers, such as wearable glove interface controller, etc. By way of example, controller input 161 may include directional inputs, button presses, trigger activation, movements, gestures or other kinds of inputs processed from the operation of a gaming controller. The audio input 162 can be processed from a microphone 151 of the HMD 102, or from a microphone included in the image capture device 108 or elsewhere within the local system environment. The motion input 163 can be processed from a motion sensor 159 included in the HMD 102, or from image capture device 108 as it captures images of the HMD 102. For example, the motion sensor 159 may include an inertial sensor configured to capture acceleration data of the HMD 102 that is associated with head movement of the user 105. In addition, image capture device 108 may be configured for head tracking to monitor head movement of the user 105. The VR content engine 111 (e.g., executing a gaming application) receives inputs which are processed according to the configuration of the game engine to update the game state of the video game. The engine 111 outputs game state data to various rendering modules which process the game state data to define content which will be presented to the user 105.

In the illustrated embodiment, a video rendering module 183 is defined to render a video stream including VR content 115, which when presented on the HMD 102 gives a user 105 a three dimensional VR experience. A lens of optics 170 in the HMD 102 is configured for viewing the VR content 115. A display screen 175 is disposed behind the lens of optics 170, such that the lens of optics 170 is between the display screen 175 and an eye 160 of the user 105, when the HMD 102 is worn by the user 105. In that manner, the video stream may be presented by the display screen/projector mechanism 175, and viewed through optics 170 by the eye 160 of the user 105. An HMD user 105 may elect to interact with the interactive VR content (e.g., VR video source, video game content, etc.) by wearing the HMD and selecting a video game for game play, for example. Interactive virtual reality (VR) scenes from the video game are rendered on the display screen 175 of the HMD. In that manner, the HMD allows the user 105 to completely immerse in the game play by provisioning display mechanism of the HMD in close proximity to the user's eyes. The display regions defined in the display screen of the HMD for rendering content may occupy large portions or even the entirety of the field of view of the user 105. Typically, each eye is supported by an associated lens of optics 170 which is viewing one or more display screens.

An audio rendering module 182 is configured to render an audio stream for listening by the user 105. In one embodiment, the audio stream is output through a speaker 152 associated with the HMD 102. It should be appreciated that speaker 152 may take the form of an open air speaker, headphones, or any other kind of speaker capable of presenting audio.

In one embodiment, a gaze tracking camera 165 is included in the HMD 102 to enable tracking of the gaze of the user 105. Although only one gaze tracking camera 165 is included, it should be noted that more than one gaze tracking camera may be employed to track the gaze of the user 105. The gaze tracking camera captures images of the user's eyes, which are analyzed to determine the gaze direction of the user 105. In one embodiment, information about the gaze direction of the user 105 can be utilized to affect the video rendering. For example, if a user's eyes are determined to be looking in a specific direction, then the video rendering for that direction can be prioritized or emphasized, such as by providing greater detail or faster updates in the region where the user 105 is looking. It should be appreciated that the gaze direction of the user 105 can be defined relative to the head mounted display, relative to a real environment in which the user 105 is situated, and/or relative to a virtual environment that is being rendered on the head mounted display.

Broadly speaking, analysis of images captured by the gaze tracking camera 192, when considered alone, provides for a gaze direction of the user 105 relative to the HMD 102. However, when considered in combination with the tracked location and orientation of the HMD 102, a real-world gaze direction of the user 105 can be determined, as the location and orientation of the HMD 102 is synonymous with the location and orientation of the user's head. That is, the real-world gaze direction of the user 105 can be determined from tracking the positional movements of the user's eyes and tracking the location and orientation of the HMD 102. When a view of a virtual environment is rendered on the HMD 102, the real-world gaze direction of the user 105 can be applied to determine a virtual world gaze direction of the user 105 in the virtual environment.

Additionally, a tactile feedback module 181 is configured to provide signals to tactile feedback hardware included in either the HMD 102 or another device operated by the HMD user 105, such as a controller 104. The tactile feedback may take the form of various kinds of tactile sensations, such as vibration feedback, temperature feedback, pressure feedback, etc.

Further, discomfort monitor 118 is configured to monitor and store discomfort and/or sickness experiences of the user 105 as the user interacts with VR content. In particular, physiological data may include measurements from physiological sensors 125 located both within HMD 102 and outside of the HMD 102 and from actuator 109, all of which collect information about the physiological state of user 105. Information relating to the discomfort of the user may be outputted from monitor 118 and delivered to the discomfort reduction filtering effect module, which is shown as a FOV throttler 590, of the VR content engine, in one embodiment. In that manner, a discomfort reduction filtering effect may be enabled (as supplied by the developer) when the input indicates that the user is experiencing discomfort. In another embodiment, the application of the discomfort reduction filtering effect may be performed in real-time as an overlay process to the VR content generated by the VR content engine in response to a discomfort input 117 that indicates that the user is experiencing discomfort. For example, an FOV throttling overlay 174 may be added to the rendered video delivered to the HMD 102.

In addition, once the discomfort input 117 indicates that the user is not experiencing discomfort, the discomfort reduction filtering effect may be disabled.

Figure 5:
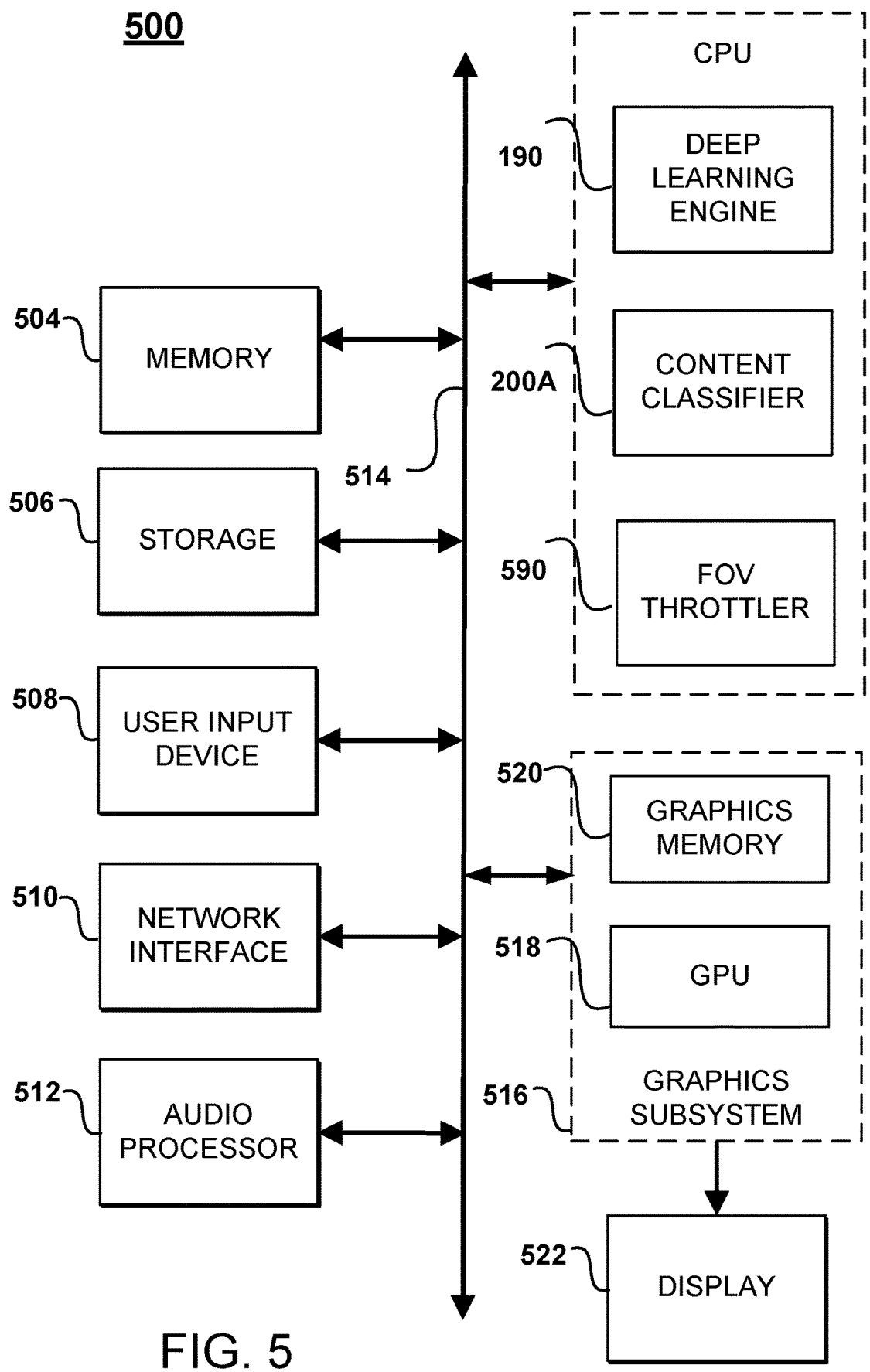
FIG. 5 illustrates components of an example device that can be used to perform aspects of the various embodiments of the present disclosure.

FIG. 5 illustrates components of an example device that can be used to perform aspects of the various embodiments of the present disclosure. For example, FIG. 5 illustrates an exemplary hardware system suitable for implementing a device in accordance with one embodiment. This block diagram illustrates a computer system 500, such as a personal computer, video game console, personal digital assistant, or other digital device, suitable for practicing an embodiment of the invention. Computer system 500 includes a central processing unit (CPU) 502 for running software applications and optionally an operating system. CPU 502 may be comprised of one or more homogeneous or heterogeneous processing cores.

In accordance with various embodiments, CPU 502 is one or more general-purpose microprocessors having one or more processing cores. Further embodiments can be implemented using one or more CPUs with microprocessor architectures specifically adapted for highly parallel and computationally intensive applications, such as media and interactive entertainment applications, of applications configured for deep learning, content classification, and user classifications. For example, CPU 502 may be configured to include deep learning engine 190 that is configured to recognize which VR content (e.g., types and/or patterns of VR content) when interacted with will cause a user to experience discomfort and/or sickness reactions. In addition, the CPU 502 may be configured to include the content classifier 200A, in which the recognition of which VR content induces discomfort and/or sickness reactions in users can be utilized to classify content according to corresponding predicted levels of discomfort and/or sickness induced by that content. Further, CPU 502 may be configured to include the FOV throttler 590, which is an implementation of a discomfort reduction filtering effect which acts to change the VR content (e.g., to give a lesser discomfort experience), and/or change the display of the VR content that is identified likely to induces discomfort and/or sickness reactions in users.

Memory 504 stores applications and data for use by the CPU 502. Storage 506 provides non-volatile storage and other computer readable media for applications and data and may include fixed disk drives, removable disk drives, flash memory devices, and CD-ROM, DVD-ROM, Blu-ray, HD-DVD, or other optical storage devices, as well as signal transmission and storage media. User input devices 508 communicate user inputs from one or more users to the computer system 500, examples of which may include keyboards, mice, joysticks, touch pads, touch screens, still or video cameras, and/or microphones. Network interface 510 allows computer system 500 to communicate with other computer systems via an electronic communications network, and may include wired or wireless communication over local area networks and wide area networks such as the Internet. An audio processor 512 is adapted to generate analog or digital audio output from instructions and/or data provided by the CPU 502, memory 504, and/or storage 506. The components of computer system 500, including CPU 502, memory 504, data storage 506, user input devices 508, network interface 510, and audio processor 512 are connected via one or more data buses 522

A graphics subsystem 514 is further connected with data bus 522 and the components of the computer system 500. The graphics subsystem 514 includes a graphics processing unit (GPU) 516 and graphics memory 518. Graphics memory 518 includes a display memory (e.g., a frame buffer) used for storing pixel data for each pixel of an output image. Graphics memory 518 can be integrated in the same device as GPU 516, connected as a separate device with GPU 516, and/or implemented within memory 504. Pixel data can be provided to graphics memory 518 directly from the CPU 502. Alternatively, CPU 502 provides the GPU 516 with data and/or instructions defining the desired output images, from which the GPU 516 generates the pixel data of one or more output images. The data and/or instructions defining the desired output images can be stored in memory 504 and/or graphics memory 518. In an embodiment, the GPU 516 includes 3D rendering capabilities for generating pixel data for output images from instructions and data defining the geometry, lighting, shading, texturing, motion, and/or camera parameters for a scene. The GPU 516 can further include one or more programmable execution units capable of executing shader programs. In one embodiment, GPU 516 may be implemented within deep learning engine 190 to provide processing power, such as for the deep learning engine 190.

The graphics subsystem 514 periodically outputs pixel data for an image from graphics memory 518 to be displayed on display device 520. Display device 520 can be any device capable of displaying visual information in response to a signal from the computer system 500, including CRT, LCD, plasma, and OLED displays. Computer system 500 can provide the display device 520 with an analog or digital signal.

It should be understood that the embodiments described herein may be executed on any type of client device. In some embodiments, the client device is a head mounted display (HMD). For example, the HMD may be used during testing of users to learn which VR content, patterns of VR content, patterns associated with the generation of or interaction with VR content, or patterns associated with simulated or tested user interactions with corresponding VR content, and/or patterns of actions taken or generated by the user in association with the generation of that VR content induces discomfort and/or sickness. Further, the HMD may be used to classify or calibrate a user according to tested discomfort and/or sickness responses to VR content (e.g., baseline VR content). The HMD may be configured to apply a discomfort reduction filtering effect to those zones in an application that are identified as having VR content, patterns of VR content, patterns associated with the generation of or interaction with VR content, or patterns associated with simulated or tested user interactions with corresponding VR content, and/or patterns of actions taken or generated by the user in association with the generation of that VR content likely to cause discomfort and/or sickness, in order to reduce any potential discomfort and/or sickness in a user.

Figure 6:
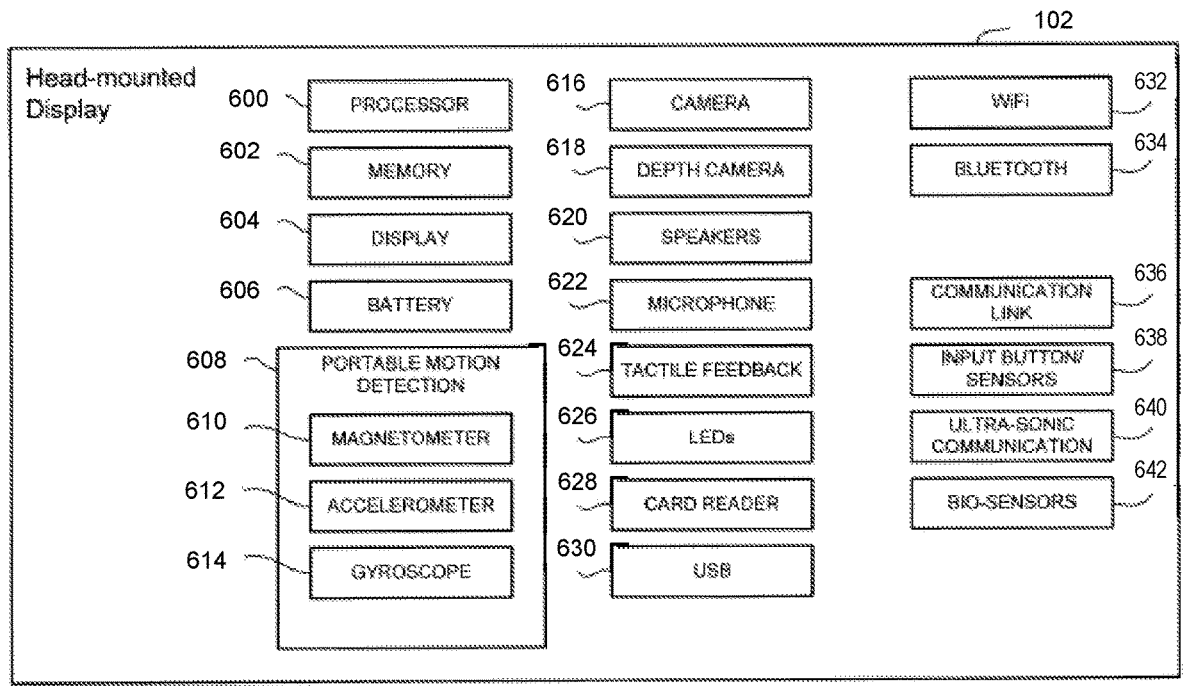
FIG. 6 is a diagram illustrating components of a head-mounted display, in accordance with one embodiment of the disclosure.

FIG. 6, a diagram illustrating components of a head-mounted display (HMD) 650 is shown, in accordance with an embodiment of the disclosure. The HMD may be used during the during a classification phase that identifies zones of VR content that are likely to induce discomfort and/or sickness, and to apply a discomfort reduction filtering effect to those zones.

The head-mounted display 650 includes a processor 600 for executing program instructions. A memory 602 is provided for storage purposes, and may include both volatile and non-volatile memory. A display 604 is included which provides a visual interface that a user may view. A battery 606 is provided as a power source for the head-mounted display 650. A motion detection module 608 may include any of various kinds of motion sensitive hardware, such as a magnetometer 610, an accelerometer 612, and a gyroscope 614.

An accelerometer is a device for measuring acceleration and gravity induced reaction forces. Single and multiple axis models are available to detect magnitude and direction of the acceleration in different directions. The accelerometer is used to sense inclination, vibration, and shock. In one embodiment, three accelerometers 612 are used to provide the direction of gravity, which gives an absolute reference for two angles (world-space pitch and world-space roll).

A magnetometer measures the strength and direction of the magnetic field in the vicinity of the head-mounted display. In one embodiment, three magnetometers 610 are used within the head-mounted display, ensuring an absolute reference for the world-space yaw angle. In one embodiment, the magnetometer is designed to span the earth magnetic field, which is ±80 microtesla. Magnetometers are affected by metal, and provide a yaw measurement that is monotonic with actual yaw. The magnetic field may be warped due to metal in the environment, which causes a warp in the yaw measurement. If necessary, this warp can be calibrated using information from other sensors such as the gyroscope or the camera. In one embodiment, accelerometer 612 is used together with magnetometer 610 to obtain the inclination and azimuth of the head-mounted display 650.

A gyroscope is a device for measuring or maintaining orientation, based on the principles of angular momentum. In one embodiment, three gyroscopes 614 provide information about movement across the respective axis (x, y and z) based on inertial sensing. The gyroscopes help in detecting fast rotations. However, the gyroscopes can drift overtime without the existence of an absolute reference. This requires resetting the gyroscopes periodically, which can be done using other available information, such as positional/orientation determination based on visual tracking of an object, accelerometer, magnetometer, etc.

A camera 616 is provided for capturing images and image streams of a real environment. More than one camera may be included in the head-mounted display 650, including a camera that is rear-facing (directed away from a user when the user is viewing the display of the head-mounted display 650), and a camera that is front-facing (directed towards the user when the user is viewing the display of the head-mounted display 650). Additionally, a depth camera 618 may be included in the head-mounted display 650 for sensing depth information of objects in a real environment.

In one embodiment, a camera integrated on a front face of the HMD may be used to provide warnings regarding safety. For example, if the user is approaching a wall or object, the user may be warned. In one embodiment, the use may be provided with an outline view of physical objects in the room, to warn the user of their presence. The outline may, for example, be an overlay in the virtual environment. In some embodiments, the HMD user may be provided with a view to a reference marker, that is overlaid in, for example, the floor. For instance, the marker may provide the user a reference of where the center of the room is, which in which the user is playing the game. This may provide, for example, visual information to the user of where the user should move to avoid hitting a wall or other object in the room. Tactile warnings can also be provided to the user, and/or audio warnings, to provide more safety for when the user wears and plays games or navigates content with an HMD.

The head-mounted display 650 includes speakers 620 for providing audio output. Also, a microphone 622 may be included for capturing audio from the real environment, including sounds from the ambient environment, speech made by the user, etc. The head-mounted display 650 includes tactile feedback module 624 for providing tactile feedback to the user. In one embodiment, the tactile feedback module 624 is capable of causing movement and/or vibration of the head-mounted display 650 so as to provide tactile feedback to the user.

LEDs 626 are provided as visual indicators of statuses of the head-mounted display 650. For example, an LED may indicate battery level, power on, etc. A card reader 628 is provided to enable the head-mounted display 650 to read and write information to and from a memory card. A USB interface 630 is included as one example of an interface for enabling connection of peripheral devices, or connection to other devices, such as other portable devices, computers, etc. In various embodiments of the head-mounted display 650, any of various kinds of interfaces may be included to enable greater connectivity of the head-mounted display 650.

A Wi-Fi module 632 is included for enabling connection to the Internet via wireless networking technologies. Also, the head-mounted display 650 includes a Bluetooth module 634 for enabling wireless connection to other devices. A communications link 636 may also be included for connection to other devices. In one embodiment, the communications link 636 utilizes infrared transmission for wireless communication. In other embodiments, the communications link 636 may utilize any of various wireless or wired transmission protocols for communication with other devices.

Input buttons/sensors 638 are included to provide an input interface for the user. Any of various kinds of input interfaces may be included, such as buttons, touchpad, joystick, trackball, etc. An ultra-sonic communication module 640 may be included in head-mounted display 650 for facilitating communication with other devices via ultra-sonic technologies.

Bio-sensors 642 are included to enable detection of physiological data from a user. In one embodiment, the bio-sensors 642 include one or more dry electrodes for detecting bio-electric signals of the user through the user's skin.

The foregoing components of head-mounted display 650 have been described as merely exemplary components that may be included in head-mounted display 650. In various embodiments of the disclosure, the head-mounted display 650 may or may not include some of the various aforementioned components. Embodiments of the head-mounted display 650 may additionally include other components not presently described, but known in the art, for purposes of facilitating aspects of the present disclosure as herein described.

It will be appreciated by those skilled in the art that in various embodiments of the disclosure, the aforementioned handheld device may be utilized in conjunction with an interactive application displayed on a display to provide various interactive functions. The exemplary embodiments described herein are provided by way of example only, and not by way of limitation.

Figure 7:
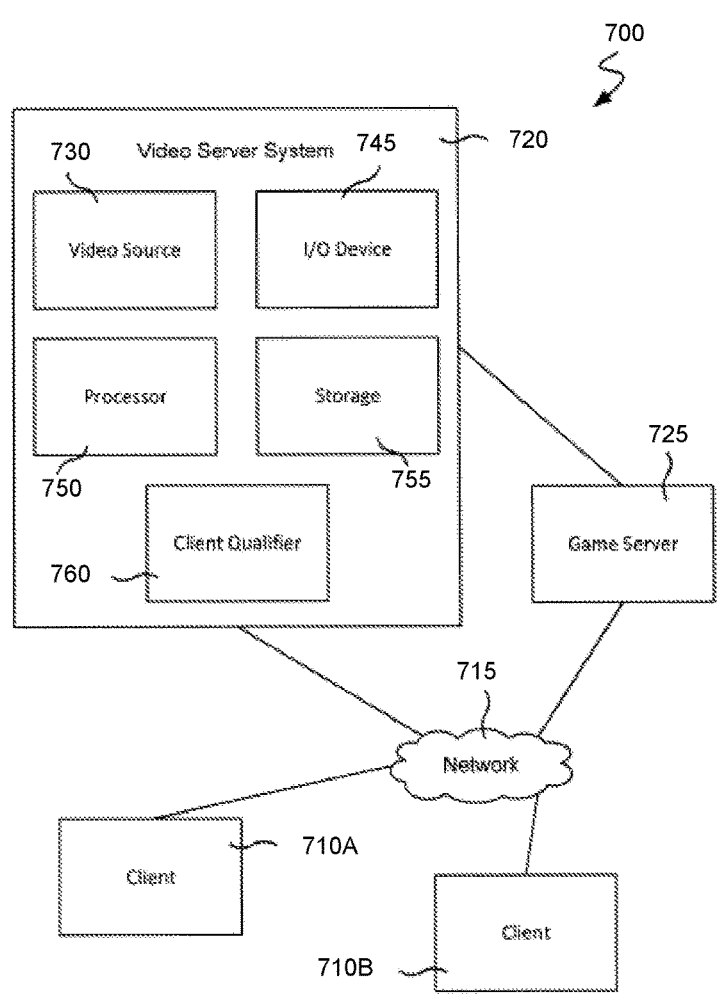
FIG. 7 is a block diagram of Game System, according to various embodiments of the disclosure. Game System is configured to provide a video stream to one or more clients via a network.

FIG. 7 is a block diagram of a Game System 700, according to various embodiments of the disclosure. Game system 700 may be used to provide VR content. Game System 700 is configured to provide a video stream to one or more Clients 710 via a Network 715. Game System 700 typically includes a Video Server System 720 and an optional game server 725. Video Server System 720 is configured to provide the video stream to the one or more Clients 710 with a minimal quality of service. For example, Video Server System 720 may receive a game command that changes the state of or a point of view within a video game, and provide Clients 710 with an updated video stream reflecting this change in state with minimal lag time. The Video Server System 720 may be configured to provide the video stream in a wide variety of alternative video formats, including formats yet to be defined. Further, the video stream may include video frames configured for presentation to a user at a wide variety of frame rates. Typical frame rates are 30 frames per second, 60 frames per second, and 120 frames per second. Although higher or lower frame rates are included in alternative embodiments of the disclosure.

Clients 710, referred to herein individually as 710A, 710B, etc., may include head mounted displays, terminals, personal computers, game consoles, tablet computers, telephones, set top boxes, kiosks, wireless devices, digital pads, stand-alone devices, handheld game playing devices, and/or the like. Typically, Clients 710 are configured to receive encoded video streams (i.e., compressed), decode the video streams, and present the resulting video to a user, e.g., a player of a game. The processes of receiving encoded video streams and/or decoding the video streams typically includes storing individual video frames in a receive buffer of the client. The video streams may be presented to the user on a display integral to Client 710 or on a separate device such as a monitor or television. Clients 710 are optionally configured to support more than one game player. For example, a game console may be configured to support two, three, four or more simultaneous players. Each of these players may receive a separate video stream, or a single video stream may include regions of a frame generated specifically for each player, e.g., generated based on each player's point of view. Clients 710 are optionally geographically dispersed. The number of clients included in Game System 700 may vary widely from one or two to thousands, tens of thousands, or more. As used herein, the term "game player" is used to refer to a person that plays a game and the term "game playing device" is used to refer to a device used to play a game. In some embodiments, the game playing device may refer to a plurality of computing devices that cooperate to deliver a game experience to the user. For example, a game console and an HMD may cooperate with the video server system 720 to deliver a game viewed through the HMD. In one embodiment, the game console receives the video stream from the video server system 720, and the game console forwards the video stream, or updates to the video stream, to the HMD for rendering.

Clients 710 are configured to receive video streams via Network 715. Network 715 may be any type of communication network including, a telephone network, the Internet, wireless networks, powerline networks, local area networks, wide area networks, private networks, and/or the like. In typical embodiments, the video streams are communicated via standard protocols, such as TCP/IP or UDP/IP. Alternatively, the video streams are communicated via proprietary standards.

A typical example of Clients 710 is a personal computer comprising a processor, non-volatile memory, a display, decoding logic, network communication capabilities, and input devices. The decoding logic may include hardware, firmware, and/or software stored on a computer readable medium. Systems for decoding (and encoding) video streams are well known in the art and vary depending on the particular encoding scheme used.

Clients 710 may, but are not required to, further include systems configured for modifying received video. For example, a client may be configured to perform further rendering, to overlay one video image on another video image, to crop a video image, and/or the like. For example, Clients 710 may be configured to receive various types of video frames, such as I-frames, P-frames and B-frames, and to process these frames into images for display to a user. In some embodiments, a member of Clients 710 is configured to perform further rendering, shading, conversion to 3-D, or like operations on the video stream. A member of Clients 710 is optionally configured to receive more than one audio or video stream. Input devices of Clients 710 may include, for example, a one-hand game controller, a two-hand game controller, a gesture recognition system, a gaze recognition system, a voice recognition system, a keyboard, a joystick, a pointing device, a force feedback device, a motion and/or location sensing device, a mouse, a touch screen, a neural interface, a camera, input devices yet to be developed, and/or the like.

The video stream (and optionally audio stream) received by Clients 710 is generated and provided by Video Server System 720. As is described further elsewhere herein, this video stream includes video frames (and the audio stream includes audio frames). The video frames are configured (e.g., they include pixel information in an appropriate data structure) to contribute meaningfully to the images displayed to the user. As used herein, the term "video frames" is used to refer to frames including predominantly information that is configured to contribute to, e.g. to effect, the images shown to the user. Most of the teachings herein with regard to "video frames" can also be applied to "audio frames."

Clients 710 are typically configured to receive inputs from a user. These inputs may include game commands configured to change the state of the video game or otherwise affect gameplay. The game commands can be received using input devices and/or may be automatically generated by computing instructions executing on Clients 710. The received game commands are communicated from Clients 710 via Network 715 to Video Server System 720 and/or Game Server 725. For example, in some embodiments, the game commands are communicated to Game Server 725 via Video Server System 720. In some embodiments, separate copies of the game commands are communicated from Clients 710 to Game Server 725 and Video Server System 720. The communication of game commands is optionally dependent on the identity of the command Game commands are optionally communicated from Client 710A through a different route or communication channel that that used to provide audio or video streams to Client 710A.

Game Server 725 is optionally operated by a different entity than Video Server System 720. For example, Game Server 725 may be operated by the publisher of a multiplayer game. In this example, Video Server System 720 is optionally viewed as a client by Game Server 725 and optionally configured to appear from the point of view of Game Server 725 to be a prior art client executing a prior art game engine. Communication between Video Server System 720 and Game Server 725 optionally occurs via Network 715. As such, Game Server 725 can be a prior art multiplayer game server that sends game state information to multiple clients, one of which is game server system 720. Video Server System 720 may be configured to communicate with multiple instances of Game Server 725 at the same time. For example, Video Server System 720 can be configured to provide a plurality of different video games to different users. Each of these different video games may be supported by a different Game Server 725 and/or published by different entities. In some embodiments, several geographically distributed instances of Video Server System 720 are configured to provide game video to a plurality of different users. Each of these instances of Video Server System 720 may be in communication with the same instance of Game Server 725. Communication between Video Server System 720 and one or more Game Server 725 optionally occurs via a dedicated communication channel. For example, Video Server System 720 may be connected to Game Server 725 via a high bandwidth channel that is dedicated to communication between these two systems.

Video Server System 720 comprises at least a Video Source 730, an I/O Device 745, a Processor 750, and non-transitory Storage 755. Video Server System 720 may include one computing device or be distributed among a plurality of computing devices. These computing devices are optionally connected via a communications system such as a local area network.

Video Source 730 is configured to provide a video stream, e.g., streaming video or a series of video frames that form a moving picture. In some embodiments, Video Source 730 includes a video game engine and rendering logic. The video game engine is configured to receive game commands from a player and to maintain a copy of the state of the video game based on the received commands. This game state includes the position of objects in a game environment, as well as typically a point of view. The game state may also include properties, images, colors and/or textures of objects.

The game state is typically maintained based on game rules, as well as game commands such as move, turn, attack, set focus to, interact, use, and/or the like. Part of the game engine is optionally disposed within Game Server 725. Game Server 725 may maintain a copy of the state of the game based on game commands received from multiple players using geographically disperse clients. In these cases, the game state is provided by Game Server 725 to Video Source 730, wherein a copy of the game state is stored and rendering is performed. Game Server 725 may receive game commands directly from Clients 710 via Network 715, and/or may receive game commands via Video Server System 720.

Video Source 730 typically includes rendering logic, e.g., hardware, firmware, and/or software stored on a computer readable medium such as Storage 755. This rendering logic is configured to create video frames of the video stream based on the game state. All or part of the rendering logic is optionally disposed within a graphics processing unit (GPU). Rendering logic typically includes processing stages configured for determining the three-dimensional spatial relationships between objects and/or for applying appropriate textures, etc., based on the game state and viewpoint. The rendering logic produces raw video that is then usually encoded prior to communication to Clients 710. For example, the raw video may be encoded according to an Adobe Flash® standard, .wav, H.264, H.263, On2, VP6, VC-1, WMA, Huffyuv, Lagarith, MPG-x. Xvid. FFmpeg, x264, VP6-8, realvideo, mp3, or the like. The encoding process produces a video stream that is optionally packaged for delivery to a decoder on a remote device. The video stream is characterized by a frame size and a frame rate. Typical frame sizes include 800×600, 1280×720 (e.g., 720p), 1024×768, although any other frame sizes may be used. The frame rate is the number of video frames per second. A video stream may include different types of video frames. For example, the H.264 standard includes a "P" frame and a "I" frame. I-frames include information to refresh all macro blocks/pixels on a display device, while P-frames include information to refresh a subset thereof. P-frames are typically smaller in data size than are I-frames. As used herein the term "frame size" is meant to refer to a number of pixels within a frame. The term "frame data size" is used to refer to a number of bytes required to store the frame.

In alternative embodiments Video Source 730 includes a video recording device such as a camera. This camera may be used to generate delayed or live video that can be included in the video stream of a computer game. The resulting video stream optionally includes both rendered images and images recorded using a still or video camera. Video Source 730 may also include storage devices configured to store previously recorded video to be included in a video stream. Video Source 730 may also include motion or positioning sensing devices configured to detect motion or position of an object, e.g., person, and logic configured to determine a game state or produce video-based on the detected motion and/or position.

Video Source 730 is optionally configured to provide overlays configured to be placed on other video. For example, these overlays may include a command interface, log in instructions, messages to a game player, images of other game players, video feeds of other game players (e.g., webcam video). In embodiments of Client 710A including a touch screen interface or a gaze detection interface, the overlay may include a virtual keyboard, joystick, touch pad, and/or the like. In one example of an overlay a player's voice is overlaid on an audio stream. Video Source 730 optionally further includes one or more audio sources.

In embodiments wherein Video Server System 720 is configured to maintain the game state based on input from more than one player, each player may have a different point of view comprising a position and direction of view. Video Source 730 is optionally configured to provide a separate video stream for each player based on their point of view. Further, Video Source 730 may be configured to provide a different frame size, frame data size, and/or encoding to each of Client 710. Video Source 730 is optionally configured to provide 3-D video and/or immersive 360 degree encoded video.

I/O Device 745 is configured for Video Server System 720 to send and/or receive information such as video, commands, requests for information, a game state, gaze information, device motion, device location, user motion, client identities, player identities, game commands, security information, audio, and/or the like. I/O Device 745 typically includes communication hardware such as a network card or modem. I/O Device 745 is configured to communicate with Game Server 725, Network 715, and/or Clients 710.

Processor 750 is configured to execute logic, e.g. software, included within the various components of Video Server System 720 discussed herein. For example, Processor 750 may be programmed with software instructions in order to perform the functions of Video Source 730, Game Server 725, and/or a Client Qualifier 760. Video Server System 720 optionally includes more than one instance of Processor 750. Processor 750 may also be programmed with software instructions in order to execute commands received by Video Server System 720, or to coordinate the operation of the various elements of Game System 700 discussed herein. Processor 750 may include one or more hardware device. Processor 750 is an electronic processor.

Storage 755 includes non-transitory analog and/or digital storage devices. For example, Storage 755 may include an analog storage device configured to store video frames. Storage 755 may include a computer readable digital storage, e.g. a hard drive, an optical drive, or solid state storage. Storage 715 is configured (e.g. by way of an appropriate data structure or file system) to store video frames, artificial frames, a video stream including both video frames and artificial frames, audio frame, an audio stream, and/or the like. Storage 755 is optionally distributed among a plurality of devices. In some embodiments, Storage 755 is configured to store the software components of Video Source 730 discussed elsewhere herein. These components may be stored in a format ready to be provisioned when needed.

Video Server System 720 optionally further comprises Client Qualifier 760. Client Qualifier 760 is configured for remotely determining the capabilities of a client, such as Clients 710A or 710B. These capabilities can include both the capabilities of Client 710A itself as well as the capabilities of one or more communication channels between Client 710A and Video Server System 720. For example, Client Qualifier 760 may be configured to test a communication channel through Network 715.

Client Qualifier 760 can determine (e.g., discover) the capabilities of Client 710A manually or automatically. Manual determination includes communicating with a user of Client 710A and asking the user to provide capabilities. For example, in some embodiments, Client Qualifier 760 is configured to display images, text, and/or the like within a browser of Client 710A. In one embodiment, Client 710A is an HMD that includes a browser. In another embodiment, client 710A is a game console having a browser, which may be displayed on the HMD. The displayed objects request that the user enter information such as operating system, processor, video decoder type, type of network connection, display resolution, etc. of Client 710A. The information entered by the user is communicated back to Client Qualifier 760.

Automatic determination may occur, for example, by execution of an agent on Client 710A and/or by sending test video to Client 710A. The agent may comprise computing instructions, such as java script, embedded in a web page or installed as an add-on. The agent is optionally provided by Client Qualifier 760. In various embodiments, the agent can find out processing power of Client 710A, decoding and display capabilities of Client 710A, lag time reliability and bandwidth of communication channels between Client 710A and Video Server System 720, a display type of Client 710A, firewalls present on Client 710A, hardware of Client 710A, software executing on Client 710A, registry entries within Client 710A, and/or the like.

Client Qualifier 760 includes hardware, firmware, and/or software stored on a computer readable medium. Client Qualifier 760 is optionally disposed on a computing device separate from one or more other elements of Video Server System 720. For example, in some embodiments, Client Qualifier 760 is configured to determine the characteristics of communication channels between Clients 710 and more than one instance of Video Server System 720. In these embodiments the information discovered by Client Qualifier can be used to determine which instance of Video Server System 720 is best suited for delivery of streaming video to one of Clients 710.

The following applications provide information on HMDs and motion sickness, including: commonly assigned, co-pending U.S. patent application Ser. No. 14/206,219, entitled "SWITCHING MODE OF OPERATION IN A HEAD MOUNTED DISPLAY," filed on Mar. 12, 2014; commonly assigned, co-pending U.S. patent application Ser. No. 14/712,575, entitled "SENSORY STIMULUS MANAGEMENT IN HEAD MOUNTED DISPLAY," filed on May 14, 2015; commonly assigned, co-pending U.S. patent application Ser. No. 14/615,115, entitled "MOTION SICKNESS MONITORING AND APPLICATION OF SUPPLEMENTAL SOUND TO COUNTERACT SICKNESS," filed on Feb. 5, 2015; and commonly assigned, co-pending U.S. patent application Ser. No. 14/627,406, entitled "SCANNING DISPLAY SYSTEM IN HEAD-MOUNTED DISPLAY FOR VIRTUAL REALITY," filed on Feb. 20, 2015; all of which are hereby incorporated by reference in its entirety. More information on the deep learning process implemented in some embodiments of the present invention is provided in "Introduction to Machine Learning," Second Edition, Ethem Alpaydin, Massachusetts Institute of Technology, 2010, which is hereby incorporated by reference in its entirety.

While specific embodiments have been provided for building models configured to recognize which VR content induces user discomfort and/or sickness, to classify zones in VR content based on predicted user discomfort and/or sickness, and to apply a discomfort reduction filtering effect to those zones to reduce discomfort and/or sickness of a user when viewing VR content, these are described by way of example and not by way of limitation. Those skilled in the art having read the present disclosure will realize additional embodiments falling within the spirit and scope of the present disclosure.

It should be understood that the various embodiments defined herein may be combined or assembled into specific implementations using the various features disclosed herein. Thus, the examples provided are just some possible examples, without limitation to the various implementations that are possible by combining the various elements to define many more implementations. In some examples, some implementations may include fewer elements, without departing from the spirit of the disclosed or equivalent implementations.

Embodiments of the present disclosure may be practiced with various computer system configurations including hand-held devices, microprocessor systems, microprocessor-based or programmable consumer electronics, minicomputers, mainframe computers and the like. Embodiments of the present disclosure can also be practiced in distributed computing environments where tasks are performed by remote processing devices that are linked through a wire-based or wireless network.

With the above embodiments in mind, it should be understood that embodiments of the present disclosure can employ various computer-implemented operations involving data stored in computer systems. These operations are those requiring physical manipulation of physical quantities. Any of the operations described herein that form part of embodiments of the present disclosure are useful machine operations. Embodiments of the invention also relate to a device or an apparatus for performing these operations. The apparatus can be specially constructed for the required purpose, or the apparatus can be a general-purpose computer selectively activated or configured by a computer program stored in the computer. In particular, various general-purpose machines can be used with computer programs written in accordance with the teachings herein, or it may be more convenient to construct a more specialized apparatus to perform the required operations.

The disclosure can also be embodied as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing disclosure has been described in some detail for purposes of clarity of understanding, it will be apparent that certain changes and modifications can be practiced within the scope of the appended claims. Accordingly, the present embodiments are to be considered as illustrative and not restrictive, and embodiments of the present disclosure is not to be limited to the details given herein, but may be modified within the scope and equivalents of the appended claims.

What is claimed is:

1. A method comprising:
executing an application to generate a virtual reality (VR) content for display in association with user interaction by a user, wherein the VR content provides a view into a virtual environment;
determining that the VR content includes movement of the view in the virtual environment that will cause orientation discomfort to the user;
determining that a rate of head movement of the user corresponding to the movement of the view exceeds a threshold; and
applying a discomfort reduction filter effect to the view by reducing a size of a field of view (FOV) for the view during a portion of the movement of the view when the rate of head movement of the user exceeds the threshold,
wherein there is a non-linear reduction in the size of the FOV as the rate of head movement of the user increases.

2. The method of claim 1, wherein the determining that the VR content includes the movement of the view in the virtual environment includes:
matching the VR content to at least one of a plurality of learned patterns identified through deep learning as likely to cause discomfort in users.

3. The method of claim 1, further comprising:
increasing the FOV after a sequence of images corresponding to the movement of the view in the virtual environment that will cause the orientation discomfort to the user has been displayed.

4. The method of claim 1,
wherein the user interaction includes the head movement of the user, or
wherein the user interaction includes controller input provided by the user.

5. The method of claim 4,
wherein the controller input controls a character within the virtual environment,
wherein the view into the virtual environment is a viewpoint of the character.

6. The method of claim 1, further comprising:
increasing a magnitude of the discomfort reduction filter effect based on an identified severity of the orientation discomfort to the user.

7. The method of claim 1, further comprising:
tracking gaze of the user viewing the VR content, wherein the gaze is directed to a clarity region in the FOV of the VR content displayed to the user in a head mounted display (HMD), the clarity region having a first resolution, the FOV having a periphery region outside of the clarity region having a second resolution that is lower than the first resolution;
detecting the gaze of the user is moving; and
updating a position of the clarity region of a current FOV based on the gaze of the user.

8. The method of claim 7, further comprising:
reducing a size of the clarity region in a corresponding FOV while the gaze is moving.

9. The method of claim 7, further comprising:
reducing the size of the FOV while the gaze is moving.

10. The method of claim 7, further comprising:
moving the FOV of the user with movement of the gaze.

11. A non-transitory computer-readable medium storing a computer program, the computer-readable medium comprising:
program instructions for executing an application to generate a virtual reality (VR) content for display in association with user interaction by a user, wherein the VR content provides a view into a virtual environment;
program instructions for determining that the VR content includes movement of the view in the virtual environment that will cause orientation discomfort to the user;
program instructions for determining that a rate of head movement of the user corresponding to the movement of the view exceeds a threshold; and
program instructions for applying a discomfort reduction filter effect to the view by reducing a size of a field of view (FOV) for the view during a portion of the movement of the view when the rate of head movement of the user exceeds the threshold,
wherein there is a non-linear reduction in the size of the FOV as the rate of head movement of the user increases.

12. The non-transitory computer-readable medium of claim 11, wherein the program instructions for determining that the VR content includes movement of the view in the virtual environment includes:
  program instructions for matching the VR content to at least one of a plurality of learned patterns identified through deep learning as likely to cause discomfort in users.

13. The non-transitory computer-readable medium of claim 11,
  wherein the user interaction includes the head movement of the user, or
  wherein the user interaction includes controller input provided by the user.

14. The non-transitory computer-readable medium of claim 13,
  wherein the controller input controls a character within the virtual environment,
  wherein the view into the virtual environment is a viewpoint of the character.

15. The non-transitory computer-readable medium of claim 11, further comprising:
  program instructions for tracking gaze of the user viewing the VR content, wherein the gaze is directed to a clarity region in the FOV of the VR content displayed to the user in a head mounted display (HMD), the clarity region having a first resolution, the FOV having a periphery region outside of the clarity region having a second resolution that is lower than the first resolution;
  program instructions for detecting the gaze of the user is moving; and
  program instructions for updating a position of the clarity region of a current FOV based on the gaze of the user.

16. The non-transitory computer-readable medium of claim 15, further comprising:
  program instructions for reducing a size of the clarity region in a corresponding FOV while the gaze is moving.

17. A computer system comprising:
  a processor; and
  memory coupled to the processor and having stored therein instructions that, if executed by the computer system, cause the computer system to execute a method, the method comprising:
    executing an application to generate a virtual reality (VR) content for display in association with user interaction by a user, wherein the VR content provides a view into a virtual environment;
    determining that the VR content includes movement of the view in the virtual environment that will cause orientation discomfort to the user;
    determining that a rate of head movement of the user corresponding to the movement of the view exceeds a threshold; and
    applying a discomfort reduction filter effect to the view by reducing a size of a field of view (FOV) for the view during a portion of the movement of the view when the rate of head movement of the user exceeds the threshold,
    wherein there is a non-linear reduction in the size of the FOV as the rate of head movement of the user increases.

18. The computer system of claim 17, wherein the determining that the VR content includes the movement of the view in the virtual environment in the method includes:
  matching the VR content to at least one of a plurality of learned patterns identified through deep learning as likely to cause discomfort in users.

19. The computer system of claim 17,
  wherein in the method the user interaction includes the head movement of the user, or
  wherein in the method the user interaction includes controller input provided by the user.

20. The computer system of claim 17, the method further comprising:
  tracking gaze of the user viewing the VR content, wherein the gaze is directed to a clarity region in the FOV of the VR content displayed to the user in a head mounted display (HMD), the clarity region having a first resolution, the FOV having a periphery region outside of the clarity region having a second resolution that is lower than the first resolution;
  detecting the gaze of the user is moving; and
  updating a position of the clarity region of a current FOV based on the gaze of the user.

* * * * *